US006982315B2

(12) United States Patent
Rudolph et al.

(10) Patent No.: US 6,982,315 B2
(45) Date of Patent: Jan. 3, 2006

(54) PROCESS FOR THE PREPARATION OF CARBOXAMIDES

(75) Inventors: Joachim Rudolph, Guilford, CT (US); Günther Jung, Tubingen (DE); Bernd Thern, Tubingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 372 days.

(21) Appl. No.: 10/108,667

(22) Filed: Mar. 27, 2002

(65) Prior Publication Data
US 2002/0193594 A1 Dec. 19, 2002

(30) Foreign Application Priority Data

| Mar. 28, 2001 | (DE) | 101 15 213 |
| May 31, 2001 | (DE) | 101 26 431 |
| Nov. 26, 2001 | (DE) | 101 57 882 |

(51) Int. Cl.
*C07K 1/00* (2006.01)
*C07K 1/02* (2006.01)
*C07K 1/04* (2006.01)
*C07K 1/10* (2006.01)

(52) U.S. Cl. .................. 530/333; 530/334; 530/338

(58) Field of Classification Search ......... 530/333–338, 530/317, 342; 514/2

See application file for complete search history.

(56) References Cited

U.S. PATENT DOCUMENTS

| 5,948,693 A | * | 9/1999 | Rich et al. .................. 436/518 |
| 6,384,186 B2 | * | 5/2002 | Anke et al. .................. 530/317 |
| 6,512,092 B2 | * | 1/2003 | Falb et al. .................. 530/333 |
| 2001/0008634 A1 | | 7/2001 | Anke et al. .................. 424/405 |

FOREIGN PATENT DOCUMENTS

| GB | 2049686 | 12/1980 | ............... 544/172 |
| WO | 9720857 | 6/1997 | ............... 424/405 |
| WO | 0002898 | 1/2000 | ............... 530/333 |

OTHER PUBLICATIONS

Merrifield RB. Solid–Phase Peptide Synthesis in Advances in enzymology and related areas of molecular biology, vol. 32. Nord FF, editor. 1969, John Wiley and Sons, Inc., New York. pp. 222–223.*
Wellings DA and Atherton E. Standard Fmoc Protocols. Methods in Enzymology, vol. 289. 1997, pp. 44–67.*
Nefzi A, Ostresh JM, and Houghten RA. Solid phase synthesis of mixture–based acyclic and heterocyclic small molecule combinatorial libraries from resin–bound polyamides. Biopolymers, 2001, vol. 60, pp. 212–219.*
Wipf P and Henninger TC. Solid–phase synthesis of peptide mimetics with (E)–alkene amide bond replacements derived from alkenylaziridines. Journal of Organic Chemistry, 1997, vol. 62, pp. 1586–1587.*
Thieriet N, Guibe F, and Albericio F. Solid–phase peptide synthesis in the reverse (N –>C) direction. Organic Letters, 2000, vol. 2, pp. 1815–1817.*
Gruner Saw, Keri G, Schwab R, Venetianer A, and Kessler H. Sugar amino acid containing somatostatin analogues that induce apoptosis in both drug–sensitive and multidrug–resistant tumor cells. Organic Letters, 2001, vol. 3, pp. 3723–3725.*
Li W and Yan B. Effects of polymer supports on the kinetics of solid–phase organic reactions: a comparison of polystyrene– and TentaGel–based resins. Journal of Organic Chemistry, 1998, vol. 63, pp. 4092–4097.*
Thern B, Rudolph J, Jung G. Total synthesis of the nematicidal cyclodecapeptide Omphalotin A by using racemization–free triphosgene–mediated couplings in the solid phase. Angewandte Chemie International Edition, 2002, vol. 41, pp. 2307–2309.*
Carpino, L., El–Faham, A., "The Diisopropylcarbodiimide/1–Hydroxy–7–azabenzotriazole System: Segment Coupling and Stepwise Assembly", Tetrahedron, 55: 6813–6830 (1999).
Humphrey, J., Chamberlin, A., "Chemical Synthesis of Natural Product Peptides: Coupling Methods For The Incorporation of Noncoded Amino Acids into Peptides", Chem. Rev., 97: 2243–2266 (1997).
Wenger, R., "Synthesis of Cyclosporine, Part II", Chimica Acta, 66: 2672–2702 (1983).
Colucci, W., Tung, R., Petri, J., Rich, D., "Synthesis of D–Lysine$^8$–cyclosporine A Further Characterization of BOP–C1 in the 207 Hexapeptide Fragment Synthesis", J. Org. Chem., 55: 2895–2903 (1990).
Raman, P., Stokes, S., Angell, Y., Flentke, G., Rich, D., "Methods to Circumvent a Difficult Coupling in the Solid–Phase Synthesis of Cyclosporine Analogues", J. Org. Chem., 63: 5734–5735 (1998).
Li, P., Xu, J., "A Novel Thiazolium Type Peptide Coupling Reagent for Hindered Amino Acids", Tetrahedron Lett., 40: 8301–8304 (1999).
Li, P., Xu, J., "2–Bromo–1–ethyl Pyridinium Tetrafluoroborate (BEP): A Powerful Coupling Reagent for N–Methylated Peptide Synthesis", Chem. Lett. 2000, 204–205.

(Continued)

Primary Examiner—Bruce R. Campell
Assistant Examiner—Andrew D. Kosar

(57) ABSTRACT

The invention relates to a process for the preparation of carboxamides, in particular peptides, from an acid component in the form of a compound containing at least one carboxyl group and an amine component in the form of a compound containing at least one primary or secondary amino group, and its use.

26 Claims, 12 Drawing Sheets

OTHER PUBLICATIONS

Figure 1:
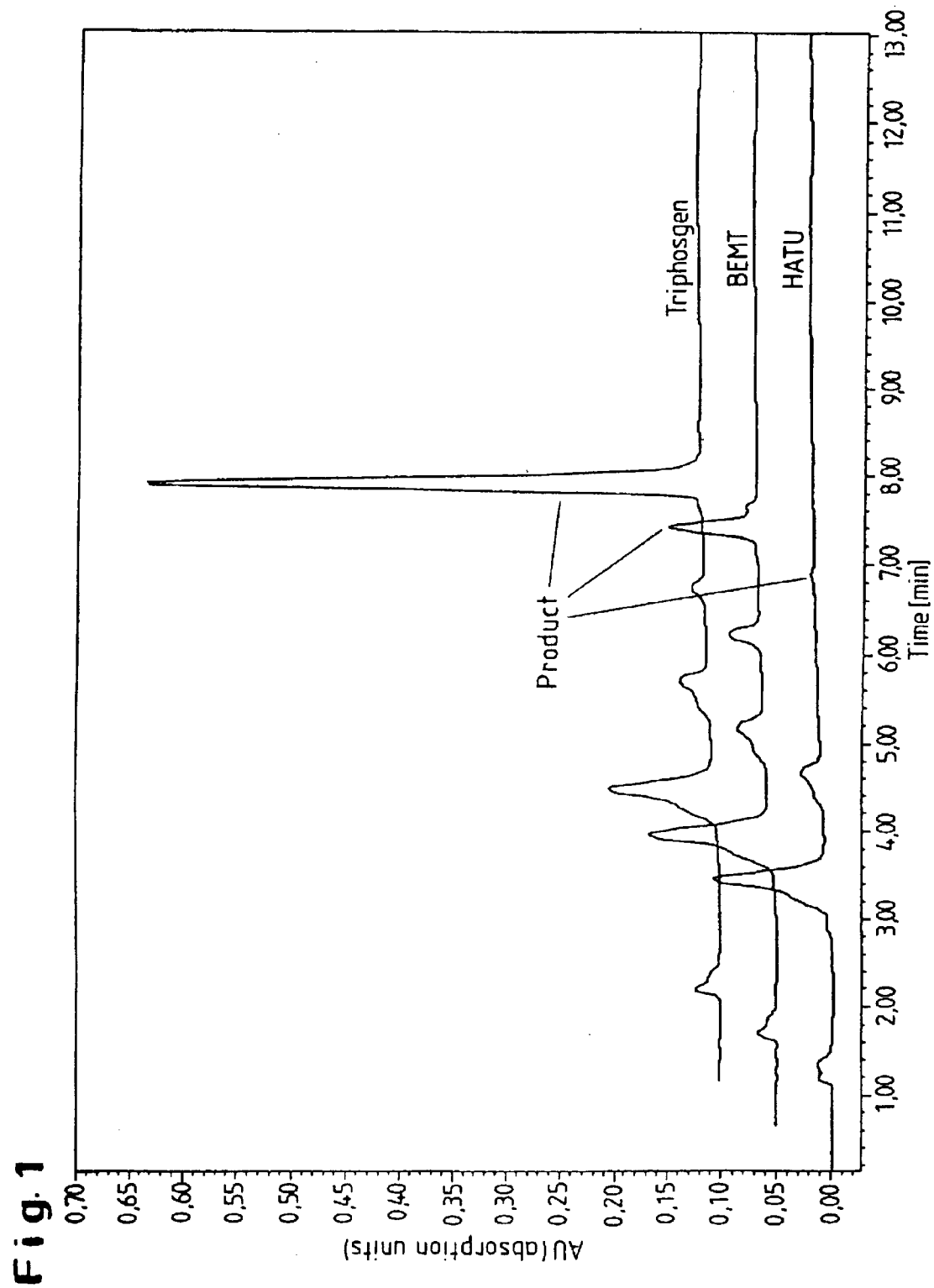

Li, P., Xu, J., "Total Synthesis of Cyclosporin O Both in Solution and in the Solid Phase Using Novel Thiazolium–, Immonium–, and Pyridinium–Type Coupling Reagents: BEMT, BDMP, and BEP", J. Org. Chem., 65: 2951–2958 (2000).

Falb, E., Yechezkel, T., Salitra, Y., Gilon, C., "*In Situ* Generation of Fmoc–amino Acid Chlorides Using Bis–(trichloromethyl)carbonate and Its Utilization for Difficult Couplings in Solid–phase Peptide Synthesis", J. Peptide Res., 53: 507–517 (1999).

Urban, J., Vaisar, T., Shen, R., Lee, M., "Lability of N–alkylated Peptides Towards TFA Cleavage", Int. J. Peptide Protein Res., 47: 182–189 (1996).

Mayer, A., Anke, H., Sterner, O., "Omphalotin, A New Cyclic Peptide With Potent Nematicidal Activity From Omphalotus Olearius 1. Fermentation and Biological Activity", Nat. Prod. Lett., 10: 25–32 (1997).

Sterner, O., Etzel, W., Mayer, A., Anke, H., "Omphalotin, A New Cyclic Peptide With Potent Nematicidal Activity From Omphalotus Olearius 11. Isolation and Structure Determination", Nat. Prod. Lett., 10: 33–38 (1997).

Konig, W., Benecke, I., Lucht, N., Schmidt, E., Schulze, J., Sievers, S., "Isocyanates as Reagents for Enantiomer Separation: Application to Amino Acids, N–Methylamino Acids and 3–Hydroxy Acids", J. Chromatogr., 279: 555–564 (1983).

* cited by examiner

PROCESS FOR THE PREPARATION OF CARBOXAMIDES

The invention relates to a process for the preparation of carboxamides, in particular peptides.

Carboxamides are customarily prepared by formation of an amide bond CO—N between the carbonyl group of an acid component, e.g. a carboxylic acid, and the nitrogen atom of an amine component, e.g. a primary or secondary amine. This bond formation is also called condensation, but below is called coupling.

Coupling is of particular importance for peptide synthesis. The aim of peptide synthesis is the construction of peptides from amino acids in such a way that the desired sequence of the amino acid units is adhered to exactly, a yield (efficiency) which is as high as possible is achieved and epimerization—or racemization if only one asymmetric carbon atom is present—is largely or completely avoided during the reaction in favour of a higher product purity.

At the start is the synthesis of dipeptides, where as in all subsequent steps care is to be taken that in each case only one of the two functional groups of the amino acids (or of the peptides) reacts. By blocking the other groups in each case by means of protective groups, shown symbolically as PG" and PG' below, it is thus achieved that the acylation of the free amino group of an amino acid of the general formula AA, HN(R')—CH(R)—COOH, (R, R'=H, optionally substituted alkyl or aryl group; e.g. AA=tryptophan, lysine, asparagine, serine, etc.) can take place only through the carboxyl group of another amino acid. The first step of peptide synthesis is accordingly the synthesis of the partially protected amino acids 1, PG"-N(R'")—CH(R")—COOH, and 2, HN(R')—CH(R)—CO-PG'.

These are reacted with one another in the second step, the coupling step, for which, however, activation of the carboxyl group is necessary. To this end, this is customarily first converted in a preconnected activation step with activating reagents intermediately into a labile and particularly reactive form, usually an electron-poor species such as an anhydride, ester or halide. Nucleophilic attack of the amine component 1 is thereby favoured.

The reaction of the partially protected, activated components 1 and 2 in the coupling step in the presence of coupling reagents (condensation reagents) finally leads to the desired dipeptide PG"-N(R'")—CH(R")—CO—N(R')—CH(R)—CO-PG'.

The third step of the peptide synthesis consists in the removal of the protective groups, for which specific reagents have been introduced, e.g. treatment with hydrohalic acids and/or trifluoroacetic acid in the case of PG" protective groups such as the benzyloxycarbonyl (PG"=Cbz), the tert-butoxycarbonyl (Boc), the fluoren-9-ylmethoxycarbonyl (Fmoc), the triphenylmethyl (Trt) or the nitrobenzene-sulphenyl group (Nps). The PG' protective groups of the carboxyl group, e.g. methyl, ethyl, benzyl, 4-nitrobenzyl and tert-butyl esters, are removed similarly and also by alkaline hydrolysis.

The dipeptide isolable after removal of one or both protective groups can be employed in reaction steps to be carried out analogously as a basis for the synthesis of higher (longer) peptides. Depending on the structure of the peptide, however, it can be more advantageous to use segment couplings, e.g. to prepare a dodecapeptide—instead of consecutively in 11 coupling steps—by linkage of three tetrapeptides, or it can even be necessary to develop specific synthesis strategies.

Most peptide syntheses are carried out as solid-phase syntheses. Solid-phase synthesis and solid-phase technique are understood as meaning procedures in which at least one reaction component—in the case of peptide synthesis the acid or amine component, e.g. an amino acid or a peptide—is present in solid-phase-bound form. This takes place by immobilization of the reaction component on suitable carriers such as synthetic resins of various composition. In this process, either the carboxyl group of the amino acid or of the carboxyl terminus (in short: C terminus/terminal) of the peptide or the amino group of the amino acid or the amino terminus (in short: N terminus/terminal) of the peptide is attached to the carrier. The addition, recycling and removal of reaction products is considerably facilitated. The best-known solid-phase peptide synthesis is the Merrifield technique introduced by Merrifield and meanwhile largely automated.

In the solid-phase synthesis, the C-terminal amino acid unit of the peptide to be synthesized is customarily linked to the insoluble carrier via its carboxyl group. All functional groups of the amino acid side chains must be provided with permanent protective groups which are stable to the reaction conditions of the subsequent couplings. The temporary protective group which initially masks the α-amino group during the loading of the carrier is subsequently removed. An excess of a second amino acid is introduced, the carboxyl group of this amino acid being activated by an activating reagent for the amide bond formation. Following the coupling, the excess of reagents is removed by a washing process and the protective group of the N terminus of the dipeptide is removed before the third amino acid is added. This process is repeated until the desired peptide sequence is assembled. In a last step, the peptide is removed from the carrier and the side-chain protective groups are removed. In general, the composition of the side chains and the immobilization are co-ordinated with one another such that the protective group removal and the release of the peptide from the solid phase can be performed in one step.

Besides the solid-phase technique, the relinquishment of immobilization and change to heterogeneous mixtures such as dispersions, in particular suspensions, as far as the homogeneous phase or the combination of solid- and liquid-phase techniques is increasing.

Suitable activating reagents in the coupling of amino acids 1 and 2 where R'=R'"=H, in addition to conventional reagents for the formation of acid chlorides, mixed anhydrides, pentafluorophenyl esters etc., have proved to be combinations of various substituted carbodiimides, e.g. DCC (N,N'-dicyclohexylcarbodiimide), DIC (diisopropylcarbodiimide) or EDC (N-ethyl-N'-(3-dimethylaminopropyl)-carbodiimide.HCl), and a benzotriazole such as HOBt (1-hydroxybenzotriazole) or azabenzotriazole such as HOAt (7-aza-1-hydroxybenzotriazole).

It is known for the specific activating reagent combinations DCC/HOAt and DIC/HOAt that the use of a weak base such as collidine for the activation of the acid component and the addition of a stronger base in the coupling step can under certain circumstances considerably improve the efficiency and rate of the overall reaction (L. A. Carpino, A. El-Faham, *Tetrahedron* 1999, 55, 6813–6830).

The yield of the coupling gains considerably in importance with increasing length (size) of the peptide to the prepared. Thus a coupling yield of 95% per coupling for the preparation of a pentapeptide, starting from a first amino acid, after 4 couplings means a yield of 81%, based on the first amino acid. In the preparation of a deca-peptide, the yield after 9 couplings, however, is only 63%.

Low coupling yields mostly occur when sterically hindered amino acids make the coupling difficult. This is, for example, the case with amino acids having space-filling side chains, e.g. valine (AA: R=iso-propyl) or isoleucine (AA: R=sec-butyl), or in the case of N-alkylamino acids, i.e. amino acids having N-alkyl groups, e.g. N-methylamino acids (AA: R'=Me).

N-Alkylamino acids are constituents of a large number of biologically active peptides (J. M. Humphrey, A. R. Chamberlin, Chem. Rev. 1997, 97, 2243–2266). Although numerous highly active activating reagents such as the iminium or uronium salts derived from HOBt or HOAt, e.g. BOP—Cl or the expensive HATU, are known, as yet still no breakthrough for the problem of the solid-phase coupling of sterically hindered N-alkylamino acids has been possible. For this reason, directions were previously given for a way around this problem by using segment couplings and selective methylation on the resin, e.g. in the total synthesis of the cyclopeptide cyclosporin A, in which 7 of a total of 11 amide bonds are methylated ((a) R. M. Wenger, Helv. Chim. Acta 1983, 66, 2672; (b) W. J. Colucci, R. D. Tung, J. A. Petri, D. A. Rich, J. Org. Chem. 1990, 55, 2895; (c) P. Raman, S. S. Stokes, Y. M. Angell, G. R. Flentke, D. A. Rich, J. Org. Chem. 1998, 63, 5734–5735).

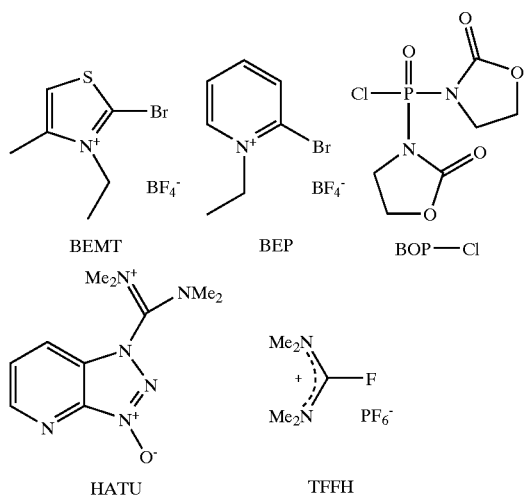

The activating reagents BEMT and BEP and their use in the total synthesis of cyclosporin O have been described by Li et al. ((a) P. Li, J. Cheng Xu, Tetrahedron Lett. 1999, 40, 8301–8304; (b) P. Li, J. Cheng Xu, Chem. Lett. 2000, 204–205; (c) P. Li, J. Cheng Xu, J. Org. Chem. 2000, 65, 2951–2958). In their use as a solid-phase activating reagent, BEMT and BEP are clearly superior to the reagent HATU, but still not efficient enough for use in the solid-phase coupling of N-methylated amino acids. Especially in the case of the coupling of two N-methylamino acids having bulky side chains, e.g. Fmoc-MeVal-OH, on MeVal-peptidyl resin, the yields of our own experiments are generally low at less than 30%.

A process for peptide synthesis using the activating reagent triphosgene and collidine known from WO 00/02898, which in the coupling of N-methylamino acids having bulky side chains affords higher coupling yields than HATU, BOP-Cl, TFFH or other reagents (E. Falb, T. Yechezkel, Y. Salitra, C. Gilon, J. Peptide Res. 1999, 53, 507–517).

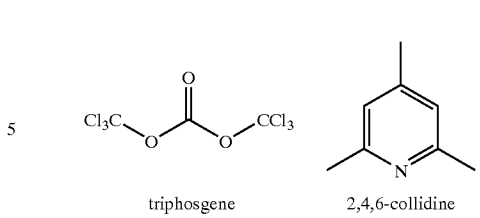

triphosgene   2,4,6-collidine

The coupling of Fmoc-protected amino acids to N-alkyl-amino acids which are bonded to a peptidyl Rink amide resin residue takes place here in the following way: An Fmoc-protected amino acid is reacted with 1.65 eq. (eq.=amounts of substance equivalent) of triphosgene and 14 eq. of collidine in THF and after an activation time of 1 min reacted with the amino acid bonded to the peptidyl resin residue for 1 h at 50° C.

This process also has a number of disadvantages. Although the coupling of sterically hindered N-methylamino acids succeeds well, the coupling yields of over 90% essential for the synthesis of higher peptides cannot be achieved. The high reaction temperature necessary is impracticable for the solid-phase synthesis and leads in an increased extent to side reactions. The Rink amide resin used needs strongly acidic cleavage conditions, which in the case of poly-N-methylated peptides lead, as is known, to decomposition (J. Urban, T. Vaisar, R. Shen, M. S. Lee, Int. J. Peptide Protein Res. 1996, 47, 182–189).

It was an object of the present invention to make available a process for the preparation of carboxamides, which makes possible the coupling of sterically hindered amino acids in high yields.

The object is achieved by a specific activating reagent in combination with the use of certain bases both together with the acid component in the activation step and together with the amine component for the coupling step.

The invention relates to a process for the preparation of carboxamides, in particular peptides, from an acid component in the form of a compound having at least one carboxyl group and an amine component in the form of a compound having at least one primary or secondary amino group, in which (i) the amine component is introduced in a solvent together with a coupling base in the form of an organic base having at least one nitrogen atom, (ii) the acid component is added to a solvent with an activating reagent in the form of a carbonate of the formula I,

$$O=C(-OX)_2 \qquad (I)$$

which contains the two identical or different, electron-withdrawing groups X which are separate or connected to one another, its monohalide of the formula II,

$$O=C(-OX)Y \qquad (II)$$

in which X has the same meaning as in formula I and Y represents a halogen atom,
or its dihalide of the formula III,

$$O=CYY' \qquad (III)$$

in which Y and Y' independently of one another each represent a halogen atom,
and an activating base in the form of an organic base having at least one nitrogen atom, (iii) the mixture containing the acid component as in (ii) is added to the mixture containing the amine component as in (i).

The process according to the invention is highly efficient and makes possible couplings which only proceeded in very low yields using the processes known hitherto and were therefore unsuitable, in particular, for the solid-phase synthesis of peptides. Thus for the first time an efficient solid- and liquid-phase synthesis of the peptides frequently occurring in nature with N-alkylated and sterically hindered amino acids is possible. The process can be carried out simply, the reaction proceeds very rapidly and is completely epimerization-free even in the case of high steric hindrance. The harmful heating during the reaction procedure can also be dispensed with. Furthermore, it allows the use of cheap coupling reagents such as triphosgene, while most of the known modern activating reagents are very expensive. Thus from an economic point of view the process according to the invention is universally suitable for the formation of amide bonds on the solid phase and in the liquid phase or solution, in fact in particular in cases in which the conventional processes for the formation of amide bonds are not efficient enough.

The present process is especially suitable for the preparation of numerous biologically active N-alkylamides, whose preparation is often problematical and needs expensive reagents. The present process is likewise suitable for the preparation of numerous N-methylated cyclopeptide biologically active natural substances, e.g. cyclosporins, tentoxins, dolastatins, jaspamides, didemnides, nodularins and a series of further representatives (J. M. Humphrey, A. R. Chamberlin, *Chem. Rev.* 1997, 97, 2243–2266). Furthermore, it can be used for functionality screening of peptides by incorporating—for the targeted suppression of certain hydrogen bridges—N-methylamino acids instead of normal non-N-alkyl-substituted amino acids. N-Methylpeptides are moreover more hydrophobic and more stable to proteolytic enzymes, which can improve their bioavailability and their therapeutic potential.

The acid component and/or the amine component is preferably an amino acid or a peptide whose other carboxyl and/or amino groups are protected.

The acid component and the amine component are customarily employed in a ratio, based on the amount of substance, of at least 1:1, preferably of 1:1 to 10:1, in particular of 1:1 to 5:1.

In a preferred embodiment of the process, either the acid component and the amine component are identical or different amino acids or the acid component is an amino acid and the amine component is a peptide or the amine component is an amino acid and the acid component is a peptide, where, above and beyond the at least one carboxyl group and the at least one primary or secondary amino group, further carboxyl and primary or secondary amino groups present are protected.

It is particularly preferred here that the amino group of the amine component is a secondary amino group and/or the amino group bonded to the α-C atom of the acid component is a secondary amino group, in particular the amino group of the amine component and the protected or peptide-linked amino group of the acid component are both N-alkylated, preferably independently of one another N-alkylated with a methyl, ethyl, propyl, iso-propyl, cyclohexyl or benzyl group or with one of these groups which is substituted by one or more amino and/or carboxyl groups, these amino groups or carboxyl groups for their part being protected by appropriate protective groups.

If the activating reagent is in the form of a carbonate of the formula I, the unit $(-OX)_2$ in the case of separate electron-withdrawing groups X is two separate groups —OX, while in the case of electron-withdrawing groups X bonded to one another, X a unit —OX—XO—, for example in a 1,3-dioxolan-2-one derivative.

The activating reagent employed is customarily a carbonate of the formula I, in which one or both groups X independently of one another represent a group $CH_{3-n}Y_n$, where n represents one of the numbers 1, 2 or 3 and $Y_n$ represents one, two or three identical or different halogen atoms, or a halogenated 1,3-dioxolan-2-one derivative, whose four hydrogen atoms in the 4- and 5-position are completely or partially substituted by one, two, three or four identical or different halogen atoms, or a mono-halide of the formula II, in which X is a group $CH_{3-n}Y_n$, where n represents one of the numbers 1, 2 or 3 and $Y_n$ represents one, two or three identical or different halogen atoms, or a dihalide of the formula III.

Preferred halogen atoms here are fluorine, chlorine and bromine, in particular chlorine, where, in the case of two or three halogen atoms bonded to a carbon atom, these are preferably identical. Accordingly, the groups X in formulae I and II independently of one another in particular represent one of the groups $CCl_3$, $CF_3$, $CBr_3$, $CHCl_2$, $CHF_2$, $CHBr_2$, $CHI_2$, $CH_2Cl$, $CH_2F$ or $CH_2Br$ and are preferably dihalides of the formula III $O=CF_2$, $O=CCl_2$ (phosgene) and $O=CBr_2$.

Preferably, the activating reagent employed is triphosgene $(O=C(-OCCl_3)_2$, bis(trichloromethyl) carbonate, BTC), diphosgene $(O=C(-OCCl_3)Cl)$, phosgene $(O=CCl_2)$ and/or 4,4,5,5-tetrachloro-1,3-dioxolan-2-one and particularly preferably triphosgene.

The acid component and the activating reagent are customarily employed in a ratio, based on the amount of substance, of at least 1:1, preferably of 1:1 to 4:1, in particular of 2:1 to 3:1. In the case of the use of triphosgene as activating reagent, a ratio of 3:1, in the case of diphosgene of 2:1 and in the case of phosgene and halogenated dioxoanones of 1:1, is particularly preferred.

The coupling base and the activating base are customarily selected independently of one another from the group comprising pyridine and the mono- or polyalkyl-substituted pyridine derivatives, preferably from the collidines, 2,4,6-tritert-butyl-pyridine, 2,6-ditert-butylpyridine, 2,6-ditert-butyl-4-methylpyridine, 2,6-dimethyl-pyridine, 2,3,5,6-tetramethylpyridine, 2-methylpyridine and pyridine, or from the group consisting of the trialkylamines, preferably from diisopropylethylamine (DIEA), triisopropylamine, N-methylmorpholine, triethylamine. The collidines are the various trimethylpyridines and ethylmethylpyridines, for example 2,3,5-collidine and in particular 2,4,6-collidine. In exactly the same way, mixtures of two or more bases can be employed.

The coupling efficiency can be increased by the specific selection of coupling and/or activating base. In a preferred embodiment of the process, the coupling base employed together with the amine component is 2,4,6-collidine, pyridine, triethyl-amine or a sterically hindered trialkylamine, preferably a sterically hindered tri-alkylamine, in particular diisopropylethylamine or triisopropylamine, particularly preferably diisopropylethylamine. In a likewise preferred embodiment of the process, the activating base employed together with the acid component is a sterically hindered mono- or polyalkyl-substituted pyridine derivative, preferably 2,4,6-collidine, 2,4,6-tritert-butylpyridine, 2,6-ditert-butylpyridine, 2,6-ditert-butyl-4-methylpyridine, 2,6- dimethylpyridine or 2,3,5,6-tetramethylpyridine, particularly preferably 2,4,6-collidine.

In a further preferred embodiment of the process, the two above preferred embodiments are combined with one another. In this case, the increase in the coupling efficiency turns out to be particularly high if a sterically hindered tri-alkylamine, in particular DIEA, as coupling base is combined with the sterically hindered pyridine derivative, preferably 2,4,6-collidine or 2,4,6-tri-tert-butyl-pyridine, in particular 2,4,6-collidine, as activating base. As a rule, 2,4,6-tri-tert-butylpyridine increases the coupling efficiency less than 2,4,6-collidine, but affords a homogeneous solution during the activation in THF.

The coupling base and/or the activating base are customarily employed in a ratio to the amine component, based on the amount of substance, of at least 2:1, preferably of 4:1 to 30:1, in particular of 8:1 to 20:1, particularly preferably of 12:1 to 16:1.

The solvents as in (i) and (ii) are selected independently of one other from the organic and inorganic solvents which are liquid under the process conditions, customarily from tetrahydrofuran, 1,4-dioxane, tetrahydropyran, ethylene glycol dimethyl ether, diethylene glycol dimethyl ether, trichloromethane, 1,3-dichloro-propane, 1,2-dichloroethane, nitromethane or a mixture of two or more thereof, preferably tetrahydrofuran, 1,4-dioxane, tetrahydropyran, ethylene glycol dimethyl ether or diethylene glycol dimethyl ether or a mixture of two or more thereof, in particular tetrahydrofuran.

Particularly preferably, the solvents as in (i) and (ii) are identical.

In a particularly preferred embodiment of the process, the coupling base employed is DIEA, the activating reagent triphosgene, the activating base 2,4,6-collidine and the solvent in each case tetrahydrofuran (THF), in particular, based on the amine component, 8 eq. of DIEA, 1.15 eq. of triphosgene and 10 eq. of 2,4,6-collidine. The acid component is in this case preferably employed in a ratio, based on the amount of substance of triphosgene, of 3:1, i.e. based on the amine component, approximately 3.5 eq. of the acid component.

The process is customarily carried out at a temperature from 15 to 30° C., preferably from 18 to 25° C., in particular from 20 to 22° C. According to (ii), 3 min are sufficient, preferably 10 s to 2 min, in particular 30 s to 1 min. After the addition as in (iii), the mixture is preferably allowed to react for a period of 5 min to 4 h. It is customarily shaken or stirred in the course of this.

In a particular embodiment of the process, the amine component or the acid component is bound reversibly to a solid-phase, preferably to a resin, in particular to a trityl resin, Wang polystyrene resin or Rink amide MBHA resin and particularly preferably to TCP resin:

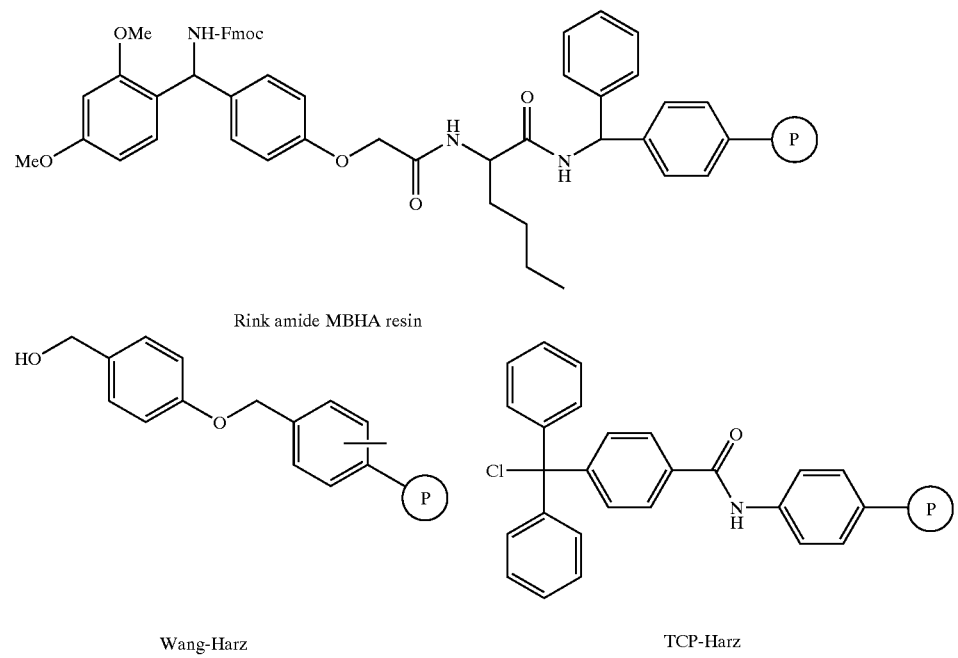

Rink amide MBHA resin

Wang-Harz

TCP-Harz

The Wang resins and Sasrin resin based on a benzyl alcohol carrier are less suitable for the coupling of sterically hindered amino acids, as at the dipeptide stage a very high tendency to form diketopiperazines can occur, which is associated with high yield losses.

Particularly suitable for the sequential synthesis of N-methylpeptides is the TCP (trityl chloride-polystyrene) resin, a trityl resin obtainable from PepChem Goldammer & Clausen (D-72076 Tübingen). The TCP resin is an outstandingly balanced resin, as far as stability and cleavability are concerned, and by means of the bulky trityl linker prevents the diketopiperazine formation at the dipeptide stage. The TCP resin is preferably contaminated hardly or even not at all, as the commercially available product obtainable from PepChem Goldammer & Clausen, with Friedel-Crafts by-products, which can prove problematic in solid-phase syntheses.

The process according to the invention is ideally suitable for the linkage of an N-methylated Fmoc-protected amino acid to an N-methylated or non-methylated amino group of a peptidyl resin.

When carrying out the process as a liquid-phase synthesis, during the activation preferably at least twice the amount of N-protected amino acid, based on the amount of substance of activating reagent, is employed in order to prevent unreacted activating reagent optionally being able to bring a subversive influence to bear on the coupling reaction.

In a particularly preferred embodiment of the liquid-phase synthesis, based on the amount of substance of amine component, (i) 1 eq. of amine component, in particular carboxyl-protected amino acid or peptide, is introduced in a solvent, in particular THF, together with a coupling base, in particular DIEA, (ii) 1.1 eq. of acid component, in particular Fmoc-protected amino acid, is added to a solvent, in particular THF, with an activating reagent, in particular triphosgene, and an activating base, in particular 2,4,6-collidine, (iii) the mixture containing the acid component as in (ii) is added to the mixture containing the amine component as in (i), coupling base and activating base being employed in an amount of at least 2 eq., preferably of 4 to 30 eq., in particular of 8 to 20 eq., particularly preferably of 12 to 16 eq., for example of 14 eq.

The liquid-phase synthesis also proceeds extremely rapidly, in high yields and epimerization-free in sterically strongly hindered cases, e.g. the coupling of MeVal with MeVal.

The present process is suitable for automation, for example in a peptide synthesizer.

EXAMPLES

Example 1

Solid-Phase Couplings Using Triphosgene

Starting from the N-methylated amino acids MeIle (Ile=L-isoleucine) or MeLeu (Leu=leucine) bound to the resin, the permethylated pentapeptide MeVal-MeVal-Sar-MeVal-MeIle (Val=L-valine, Sar=L-sarcosine) and the permethylated tetrapeptide MeLeu-MeLeu-MeVal-MeLeu were prepared by means of four or three couplings respectively and in the course of this obtained in a product purity of over 98%.

Based on the amino functions present on the resin, in each coupling the reaction was carried out using the following excesses (eq.=amounts of substance equivalent):

| | |
|---|---|
| Fmoc-amino acid: | 5 eq. |
| Triphosgene: | 1.65 eq. |
| Collidine: | 14 eq. |
| DIEA: | 14 eq. |

The concentration of the reaction solution was adjusted, relative to the Fmoc-amino acid, to 0.14 mol/l. To this end, triphosgene was prepared as a stock solution in anhydrous tetrahydrofuran (THF(abs)) by dissolving 13.7 mg of triphosgene per 1 ml of THF(abs). 7.14 ml of this solution were needed per mmol of Fmoc-amino acid.

Procedure: The dried, precoated resin (TCP resin from PepChem, coating about 0.4 mmol of amine component per g of resin) was pretreated with DIEA/THF(abs) in a plastic syringe having a plastic frit and sealing stopper. To this end, 100 mg of resin, 100 µl of THF(abs) and 100 µl of DIEA each were added to the resin. The preswelling time up to the addition of the further reagents was between 5 and 10 min.

The Fmoc-amino acid (5 eq.) was dissolved with swirling in the triphosgene/THF stock solution (1.65 eq. of triphosgene/7.14 ml per mmol of amino acid) in a polypropylene tube having a cover. As soon as the amino acid had completely dissolved, 2,4,6-collidine (14 eq./371 µl per mmol of amino acid) or 2,4,6-tri-tert-butylpyridine (14 eq.) was added, which led to the formation of a colourless precipitate in the case of collidine. The mixture was swirled for approximately 30 to 60 s in order to mix all reagents thoroughly and to activate the amino acid. The suspension was then added to the preswollen resin using a Pasteur pipette. The syringe was sealed and shaken at 20° C. for 5 to 30 minutes on a shaker. The resin was then washed successively 3 times in each case with THF, methanol (MeOH), dimethylformamide (DMF), MeOH, dichloromethane (DCM), MeOH.

Example 2

For illustration of the efficiency of the process, the following model coupling was carried out using three different coupling processes (HATU/DIEA/DCM, BEMT/DIEA/DCM and triphosgene/collidine/DIEA/THF). The model system chosen was the coupling of two sterically hindered N-methylated amino acids (MeVal), the MeVal serving as amine component being bonded to the resin (P) as a constituent of the tripeptide MeVal-MeIle-Sar. As acid component, 5 eq. of Fmoc-MeVal were used in each case and the reaction was terminated after 30 min in each case.

In the key step, the following three different coupling conditions were used:

1) HATU/DIEA/DCM, 30 min.
2) BEMT/DIEA/DCM, 30 min.
3) triphosgene/collidine/DIEA/THF, 30 min.

The dipeptide was then removed from the resin using 1% strength trifluoroacetic acid (TFA) in dichloromethane (DCM).

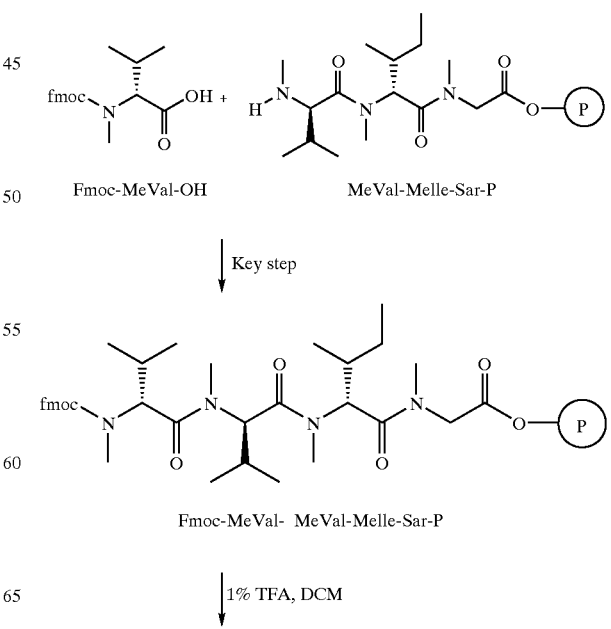

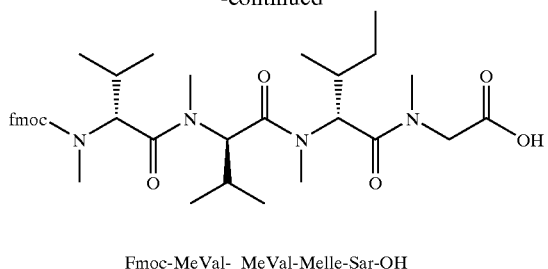

Fmoc-MeVal- MeVal-MeIle-Sar-OH

As can be seen with the aid of the HPLC chromatogram of the crude products (FIG. 1), the reagent HATU customarily employed for problem couplings leads to no conversion at all in the case indicated and the conversion with BEMT is also unsatisfactory. On the other hand, when using the process according to the invention a high conversion is achieved even after 30 min. Repetition of this coupling under the same conditions leads to quantitative product formation. In the present case, it was possible to demonstrate explicitly that no epimerization takes place, i.e. the per-L-tetrapeptide formed exclusively (see Example 3).

FIG. 1: HPLC chromatogram of the reaction products of the three reactions under various conditions (UV detection, $\lambda$=214 nm). The curves for the reactions with BEMT and triphosgene are shown shifted in perspective (i.e. the baseline of all three curves begins at 0 AU).

Example 3

Figure 2:
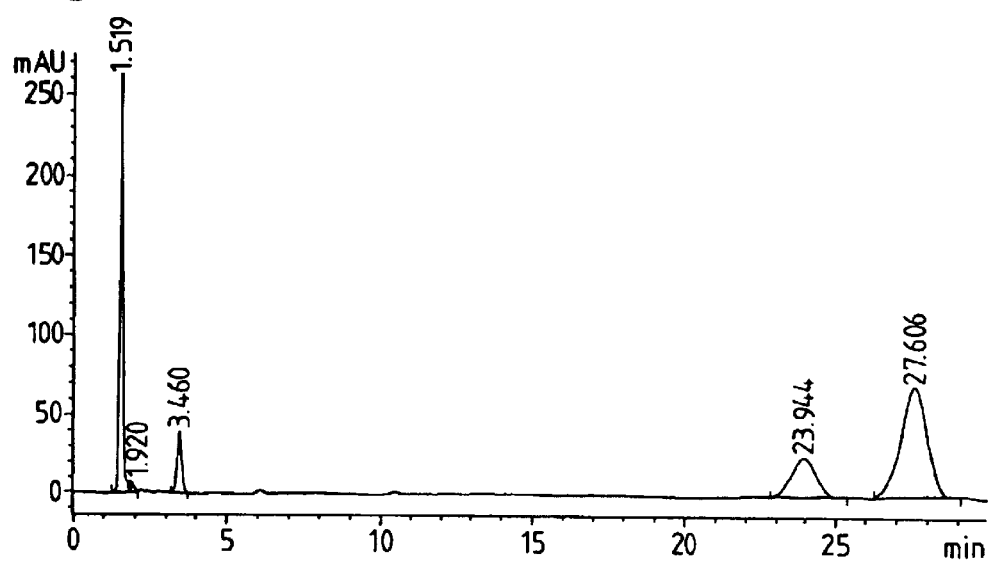

In order to find out whether epimerization has occurred in the model coupling of Example 2, a 50:50 mixture of L- and D-FmocMeVal was coupled with the tripeptide, the mixture of the two diastereomeric tetrapeptides obtained, the DLLL and LLLL isomer, was separated by means of RP-HPLC (reverse phase high-pressure liquid chromatography) and the chromatogram of the diastereomer mixture was recorded by means of UV detection (FIG. 2). The HPLC chromatograms (UV detection) of the isolated DLLL isomer (FIG. 3) and of the product of the coupling of pure L-FmocMeVal (FIG. 4) were also recorded under the same RP-HPLC conditions. In the latter case, exclusively the signal of the LLLL diastereomer was found (FIG. 4), i.e. no epimerization occurred.

FIG. 2: RP-HPLC chromatogram of a mixture of DLLL and LLLL isomer (mAU=$10^{-3}$ absorption units).

Figure 3:
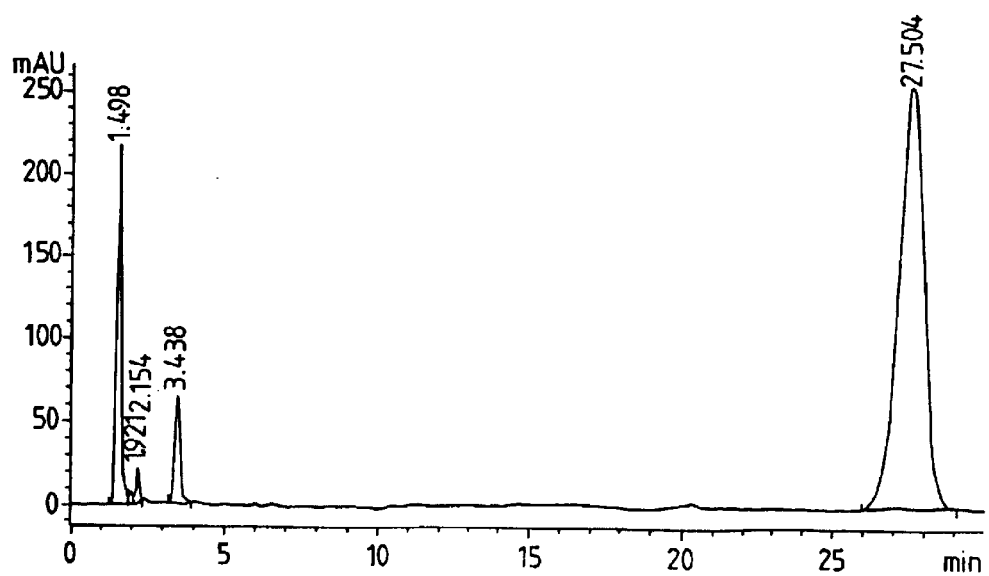

FIG. 3: RP-HPLC chromatogram of the DLLL isomer.

Figure 4:
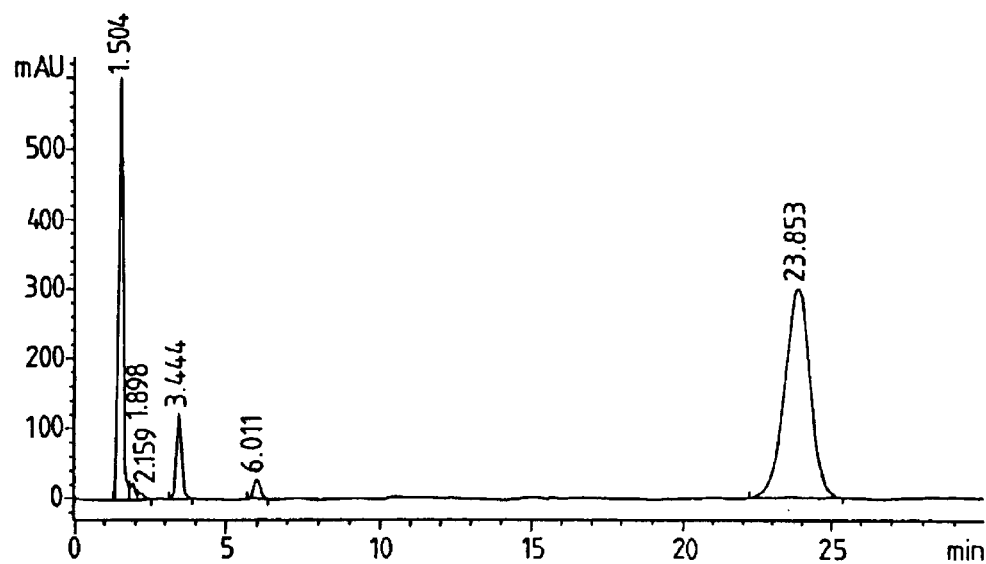

FIG. 4: RP-HPLC chromatogram of the LLLL isomer.

A) Example 4

Liquid-Phase Synthesis of a Dipeptide

The protected N-methyl-L-amino acids FmocMeVal-OH and MeVal-OBn were coupled to the dipeptide FmocMeVal-MeVal-OBn.

To this end, 1.1 eq. of the Fmoc-amino acid in THF were treated with 0.5 eq. of triphosgene in the presence of 14 eq. of 2,4,6-collidine and the resulting activation solution was added to the solution of 1 eq. of the carboxyl-protected amino acid and 14 eq. of DIEA in THF.

The reaction needed 5 min for complete reaction. Neither did by-products occurr nor did epimerization took place.

Example 5

Synthesis of Cyclosporin O

Firstly, as a precursor the linear undecapeptide having the sequence
H-Nva-Sar-MeLeu-Val-MeLeu-Ala-D-Ala-MeLeu-MeLeu-MeVal-MeLeu-(TCP resin)
was synthesized on the TCP resin and this, after removal from the resin, was cyclized to cyclosporin type O (IV).

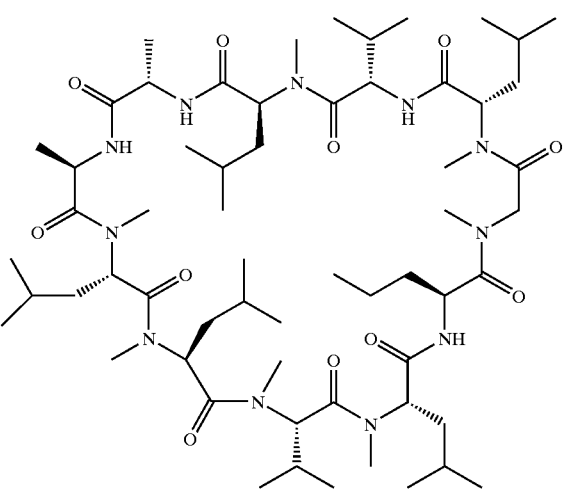

(IV)

1) Synthesis of the Linear Undecapeptide Precursor:

The coating of 150 mg of TCP resin was carried out using 55 mg of Fmoc-Leu-OH (3 eq.) in 77 µl of DCM with 3 eq. of DIEA over the course of 3 hours.

The undecapeptide was then synthesized using ten couplings. After each coupling, the chloranil test or the Kaiser test was carried out (Fmoc Solid Phase Synthesis, W. C. Chan, P. D. White (ed.) Oxford University Press, 2000, p. 61 ff.). In the case of a negative test result, coupling was carried out again.

In addition to couplings according to the invention using triphosgene as activating reagent, in special synthesis sections couplings using the activating reagent combination of diisopropylcarbodiimide (DIC) and hydroxyazobenzotriazole (HOAt) were additionally carried out. The use of these reagents took place in the following manner: 3 eq. of the N-protected amino acid were in each case dissolved in a solution of 3 eq. of HOAt and 3 eq. of DIEA in $CH_2Cl_2$. 3 eq. of DIC were added to this solution. After preactivation for 5 to 10 minutes, the reaction solution was added to the peptidyl resin. The reaction time was in each case 12 hours. The couplings with triphosgene were carried out as described in Example 1, the reaction time in each case being 2.5 or 3 hours.

The couplings were carried out in detail as follows, the activating reagent and the reaction time, inter alia, being indicated in hours:

1.) MeVal→MeLeu-(TCP resin): triphosgene, 3 h: IR checking shows Fmoc band, chloranil test positive→fresh coupling via triphosgene, 3 h: chloranil test negative
2.) MeLeu→MeVal: triphosgene, 3 h: chloranil test negative, HPLC: 100% area product peak
3.) MeLeu→MeLeu: triphosgene, 3 h: chloranil test negative, HPLC: 99% area product peak
4.) D-Ala→MeLeu: triphosgene, 3 h: chloranil test positive, HPLC: 10% area product peak→subsequent coupling with HOAt/DIC, 12 h: chloranil test negative, HPLC: 95% area product peak
5.) Ala→D-Ala: triphosgene, 3 h: Kaiser test pos. HPLC: 80% area product peak→subsequent coupling with HOAt/DIC, 12 h: Kaiser test negative, HPLC: 98% area product peak
6.) MeLeu→Ala: triphosgene, 3 h: Kaiser test negative
7.) Val→MeLeu: triphosgene, 3 h: chloranil test positive. HPLC: 60% area product peak→subsequent coupling with HOAt/DIC, 12 h: chloranil test negative
8.) MeLeu→Val: triphosgene, 3 h: Kaiser test negative
9.) Sar→MeLeu: triphosgene, 2.5 h: chloranil test negative
10.) Nva→Sar: triphosgene, 2.5 h: chloranil test negative, HPLC: 96% area product peak The tetrapeptide Fmoc-MeLeu-MeLeu-MeVal-MeLeu-OH was obtained in a purity of over 99% exclusively by means of couplings according to the invention using triphosgene, which were carried out as described in Example 1. Only the first coupling had to be repeated once in this case. The HPLC spectrum of the tetrapeptide shown in FIG. 5.

After coupling according to the invention of the 5th residue (Fmoc-D-Ala-OH) using triphosgene, the HPLC showed only 10% conversion. However, it was possible to carry out the reaction to complete conversion by additional use of HOAt/DIC coupling.

The tenth coupling shows that the coupling according to the invention using triphosgene of a non-N-methylated amino acid to an N-methylated amino acid can also proceed almost quantitatively.

Figure 6:
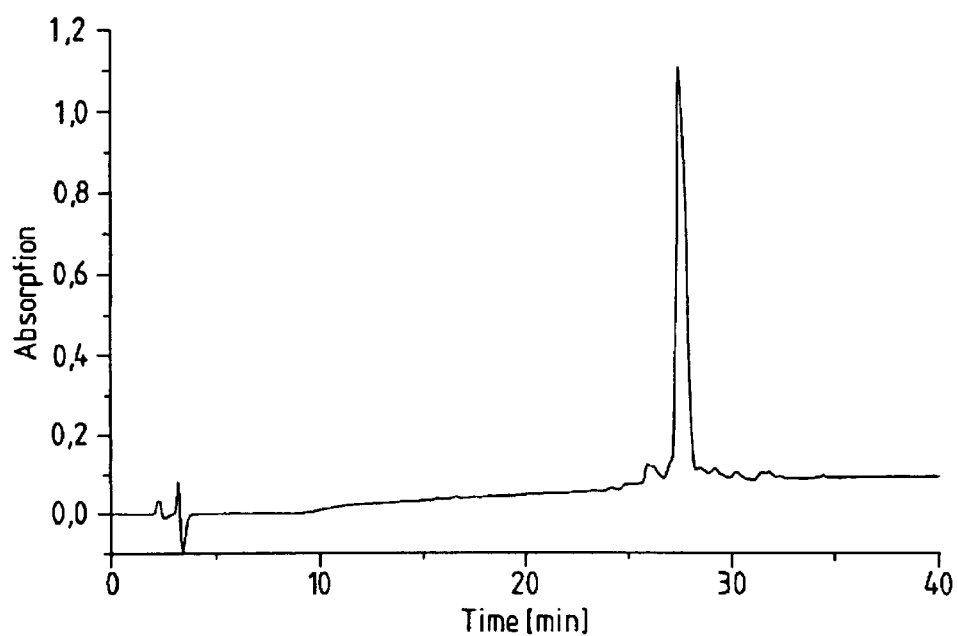

With the combination of couplings according to the invention using triphosgene and couplings using HOAt/DIC, the linear unprotected undecapeptide precursor of cyclosporin was obtained in an HPLC yield of 90% (HPLC spectrum: see FIG. 6).

2) Cyclization and Purification

Hexafluoroisopropanol was used for the removal of the linear peptide from the resin. The crude peptide was cyclized directly and without further work-up after freeze-drying. The cyclization was carried out over a period of 16 hours in dichloromethane using HOAt, EDCI and DIEA. The crude yield was about 75 to 80% (HPLC spectrum: see FIG. 7).

3) Yield Calculation and Purity Control

The coating of the resin with the first amino acid was 0.4 mmol/g of resin. 150 mg of resin were employed, which corresponds to an amount of 60 μmol of peptide on the resin (theoretical yield of linear precursor of cyclosporin O (M=1160.60) with an assumed conversion of 100% per step: 69.6 mg). After carrying out the entire sequence, a yield of linear crude product (M=1178.62) of 36.0 mg (30.5 μmol, 50.8%) was obtained.

10.0 mg (8.5 μmol) of crude product were then cyclized. The yield was 8.1 mg (7.0 μmol; 82.4%). The total yield of crude product of cyclosporin O is thus 41.8%.

The 8.1 mg of crude product obtained were purified by means of preparative HPLC, 2.9 mg (2.5 μmol; 35.7% of the crude product) being obtained. The total yield in the preparation of cyclosporin O in relation to the first resin loading was thus 14.9%.

Figure 8:
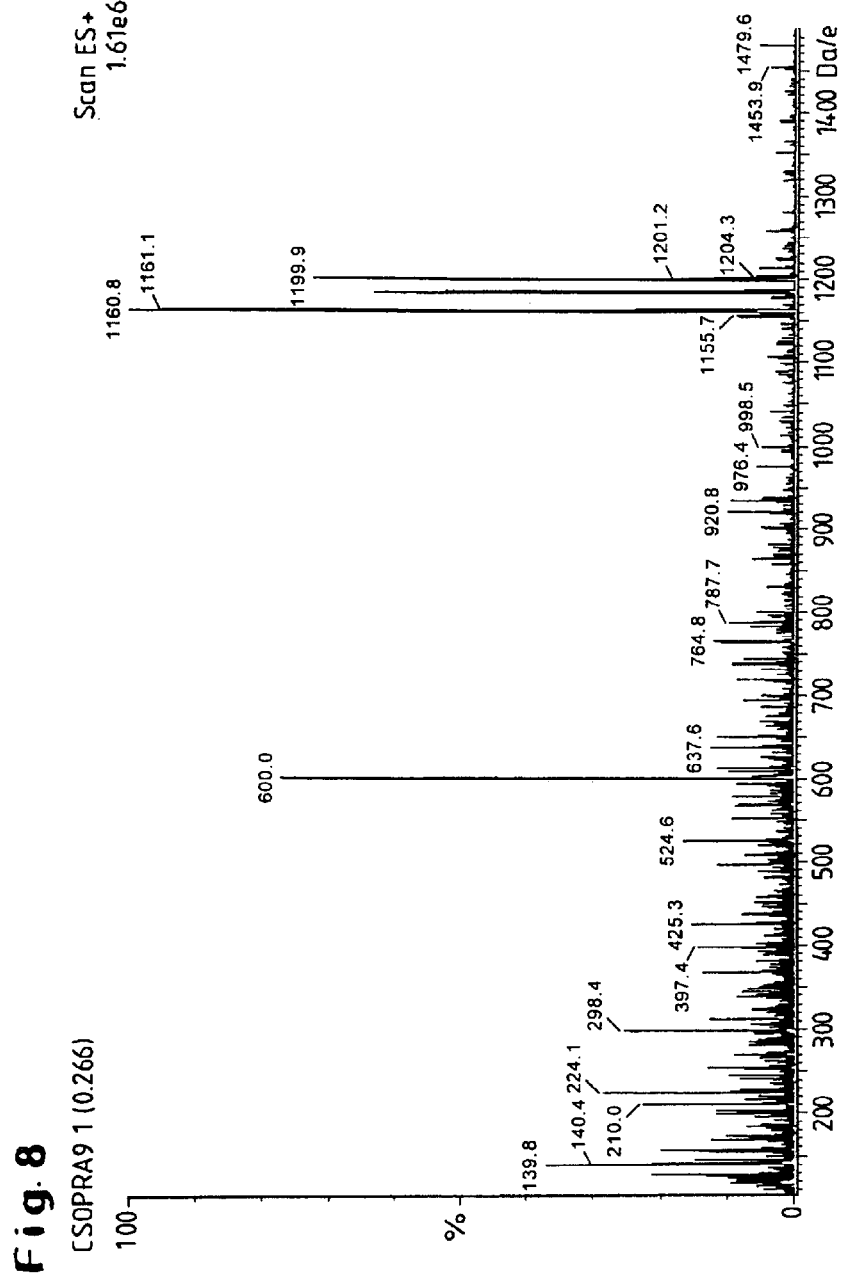

This yield is within the limits of most liquid-phase syntheses, which were obtained for various cyclosporin analogues. $^1$H-NMR confirmed the identity of the synthetic cyclosporin O with the natural substance. No diastereomers were found. The mass spectrum of the purified cyclosporin O is shown in FIG. 8.

Figure 5:
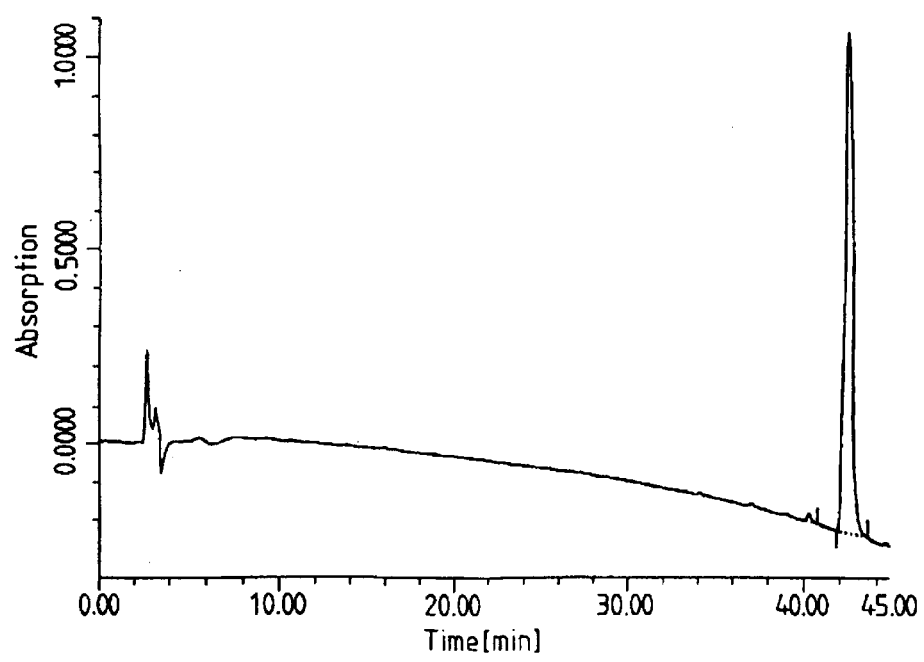

FIG. 5: HPLC chromatogram of the Fmoc-protected tetrapeptide Fmoc-MeL-MeL-MeV-MeL-OH (UV detection: λ=214 nm)

FIG. 6: HPLC chromatogram of the linear deprotected undecapeptide (UV detection: λ=214 nm)

Figure 7:
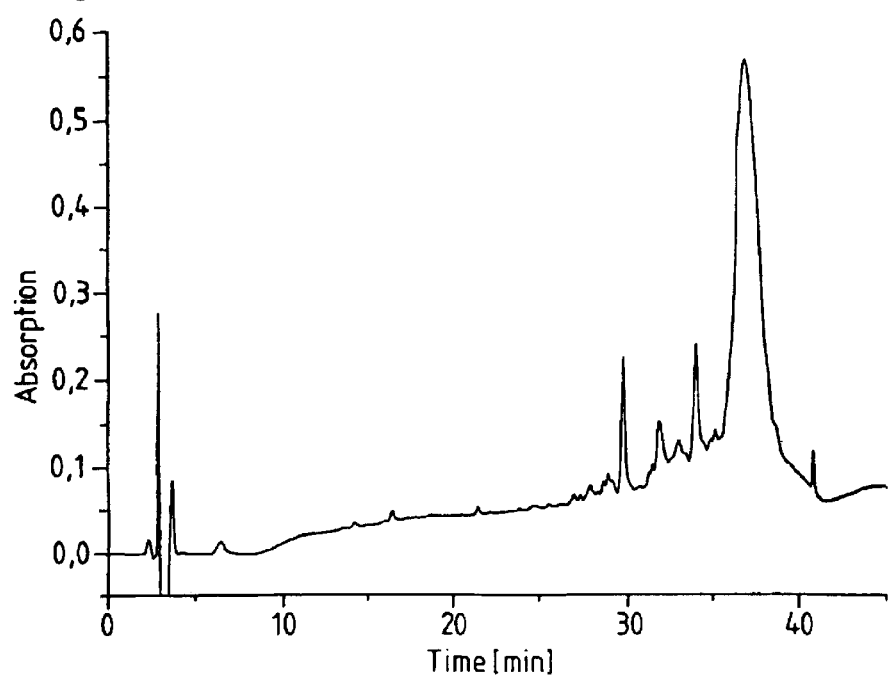

FIG. 7: HPLC chromatogram of the crude product of the cyclization reaction to cyclosporin O (UV detection: λ=214 nm).

FIG. 8: Mass spectrum of the purified cyclosporin O.

Example 6

Synthesis of Omphalotin A

The total synthesis of omphalotin A was possible for the first time using the process according to the invention. Omphalotin A is a cyclododecapeptide having a high nematicidal action, in particular against the important plant-pathogenic nematode *Meloidogyne incognita* (A. Mayer, H. Anke, O. Sterner, *Nat. Prod. Lett.* 1997, 10, 25–32; O. Sterner, W. Etzel, A. Mayer, H. Anke, *Nat. Prod. Lett.* 1997, 10, 33–38; WO 97/20857).

Firstly, as a precursor, the linear dodecapeptide having the sequence

H-Sar-Val-MeIle-Sar-Trp-MeVal-Ile-MeVal-MeVal-Sar-MeVal-MeIle-(TCP resin)

was synthesized on the TCP resin and this was cyclized, after the removal from the resin, to omphalotin A (V).

(V)

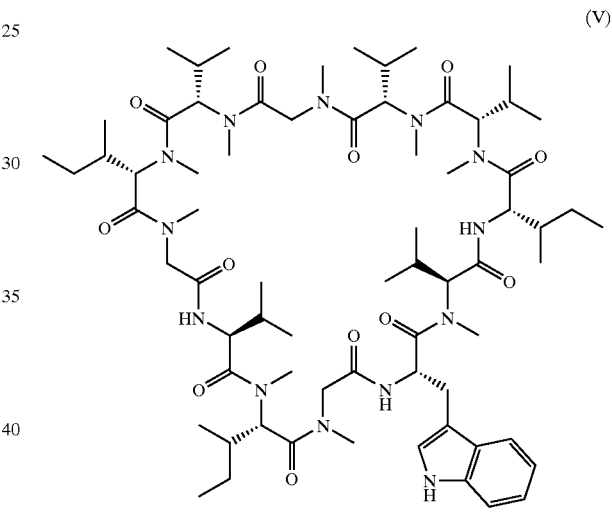

1) Synthesis of the Linear Dodecapeptide Precursor

The coating of 2 g of TCP resin was carried out with 733 mg of Fmoc-MeIle-OH (3 eq.) in 15 ml of DCM using 1 ml of DIEA (3 eq.) over the course of 3 hours. A loading of 0.56 mmol/g was determined.

The dodecapeptide was then synthesized using eleven couplings. After each coupling, the chloranil test or the Kaiser test was carried out (Fmoc Solid Phase Synthesis, W. C. Chan, P. D. White (ed.), Oxford University Press, 2000, p. 61 ff.). In the case of a negative test result, coupling was carried out again. In addition to the coupling according to the invention using triphosgene, in special synthesis sections couplings using diisopropylcarbodiimide (DIC) and hydroxyazabenzotriazole (HOAt) were carried out. The use of these reagents took place in the following manner: 3 eq. of the N-protected amino acid were dissolved in a solution of 3 eq. of HOAt and 3 eq. of DIEA in CH$_2$Cl$_2$. 3 eq. of DIC were added to this solution. After preactivation for 5–10 min, the reaction solution was added to the peptidyl resin (reaction times as indicated).

The couplings were carried out in detail as follows, the activating reagent and the reaction time, inter alia, being indicated in hours:

1.) Coupling of MeVal→MeIle: triphosgene (as Example 1), 2.5 h: chloranil test negative.
2.) Coupling of Sar→MeVal: triphosgene (as Example 1), 4 h: chloranil test negative
3.) Coupling of MeVal→Sar: triphosgene (as Example 1), 3 h: chloranil test negative
4.) MeVal→MeVal: triphosgene (as Example 1), 3 h: chloranil test negative, HPLC: 96% area product peak (after Fmoc deprotection).
5.) Ile→MeVal: HOAt/DIC, 16 h: chloranil test positive, HPLC: about 80% area product peak→subsequent coupling with HOAt/DIC, 20 h: Kaiser test negative
6.) MeVal→Ile: triphosgene (as Example 1), 1 h: Kaiser test negative, HPLC: about 95% area product peak.
7.) Trp→MeVal: HOAt, 18 h: chloranil test minimally positive, HPLC: about 93% area product peak.
8.) Sar→Trp: triphosgene (as Example 1), 1 h: Kaiser test negative, HPLC: 93% area product peak.
9.) MeIle→Sar: triphosgene (as Example 1), 1 h: chloranil test negative, HPLC: 96% area product peak.
10.) Val→MeIle: HOAt/DIC, 16 h: chloranil test positive, HPLC: 85% area product peak,→recoupling with HOAt/DIC, 15 h: chloranil test negative, HPLC: area product peak>90% (integration not possible as peak on the strike of the detector)
11.) Sar→Val: triphosgene (as Example 1), 1 h: Kaiser test negative, HPLC: 93% area product peak.
(All HPLC purities apply to Fmoc-deprotected peptides, λ=214 nm)

2) Cyclization and Purification

Hexafluoroisopropanol was used for the removal of the linear peptide from the resin. The crude peptide (HPLC spectrum: see FIG. 9, ESI mass spectrum: see FIG. 10) was cyclized directly and without further work-up after freeze-drying. 1.29 g (0.965 mmol) of crude product of linear dodecapeptide from four solid-phase runs were employed for the cyclization. The cyclization was carried out over a period of 16 hours in dichloromethane using HOAt, EDCI and DIEA. The crude yield was about 78% (HPLC spectrum: see FIG. 11).

3) Yield Calculation and Purity Control

The coating of the resin with the first amino acid was 0.56 mmol/g of resin. In total 2.0 g of resin were employed, which corresponds to an amount of 1.12 mmol of peptide on the resin (theoretical yield of linear precursor of omphalotin A (M=1318.77) with an assumed conversion of 100% per step: 1.48 g). After carrying out the entire sequence, a yield of linear crude product (M=1336.78) of 1.336 g (1.0 mmol, 89.2%) was obtained.

1.29 g (0.965 mmol) of crude product, divided into four batches of equal size, were then cyclized. The yield was 1.11 g (0.842 mmol; 87.2%). The total yield of crude product of omphalotin A is thus 77.8%.

Figure 12:
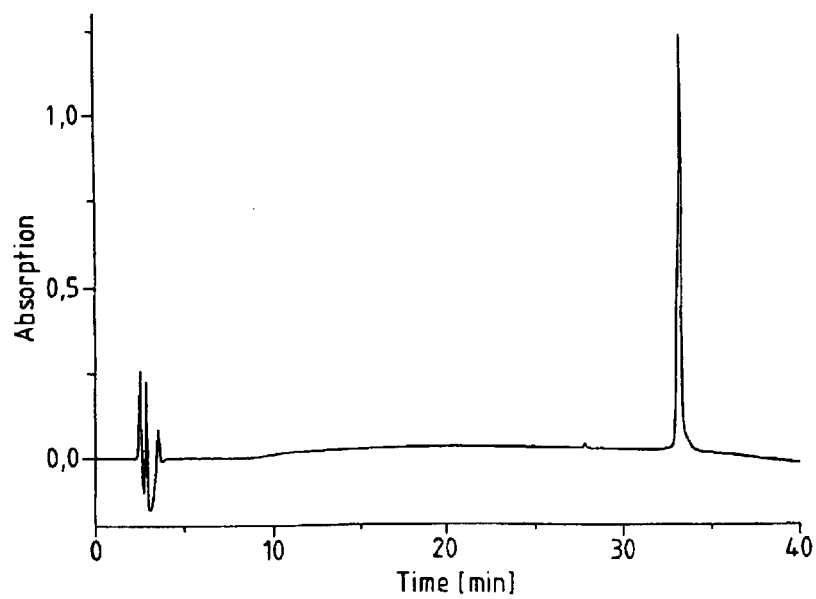

70 mg of crude product were purified by means of preparative HPLC, 24.5 mg (18.6 μmol; 35.0% of the crude product) being obtained (HPLC spectrum: see FIG. 12). The total yield in the preparation of omphalotin A in relation to the first resin loading was thus 27.2%.

$^1$H-NMR spectroscopy confirmed the identity of the synthetic omphalotin A with the natural substance (FIG. 13) (NMR data published in: O. Sterner, W. Etzel, A. Mayer, H. Anke, *Nat. Prod. Lett.* 1997, 10, 33–38). The mass spectrum of the purified omphalotin A is shown in FIG. 14.

4) Racemization Control of Omphalotin A (OmA)

The racemization tests were carried out according to the method of König (W. König, I. Benecke, N. Lucht, E. Schmidt, J. Schulze, S. Sievers, *J. Chromatogr.* 1983, 279, 555–562). To this end, after total hydrolysis of the peptide in DCl/D$_2$O, it was derivatized with isopropyl isocyanate and the derivatives were measured on a chiral GC phase using GC/MS. Hydrolysis in deuterated solvent allows the correction of the results by the amount of epimerization which was caused by the hydrolysis itself, as these derivatives contain a deuterium atom and on account of their mass, which is shifted by 1 Da, can be neglected in the GC/MS analysis.

| | N-Me-D-MeVal | N-Me-D-MeIle | N-Me-D-MeIle (Cyclization site) |
|---|---|---|---|
| Natural substance | 0.86% | 1.76% | — |
| Linear dodecapeptide | 0.66% | 0.97% | — |
| OmA crude product | 0.76% | 15.4% | about 30% |
| OmA purified | 0.31% | 6.9% | about 14% |

The analysis of the epimerization shows clearly that the coupling method per se is almost completely racemization-free. However, during the cyclization severe epimerization occurs. The wrong diastereomer formed here cannot be removed completely by column chromatography and thereby contaminates the final product (cf. HPLC chromatograms FIGS. 11 and 12, the wrong diastereomer elutes even during an isocratic run as a shoulder shortly after the omphalotin A).

Figure 9:
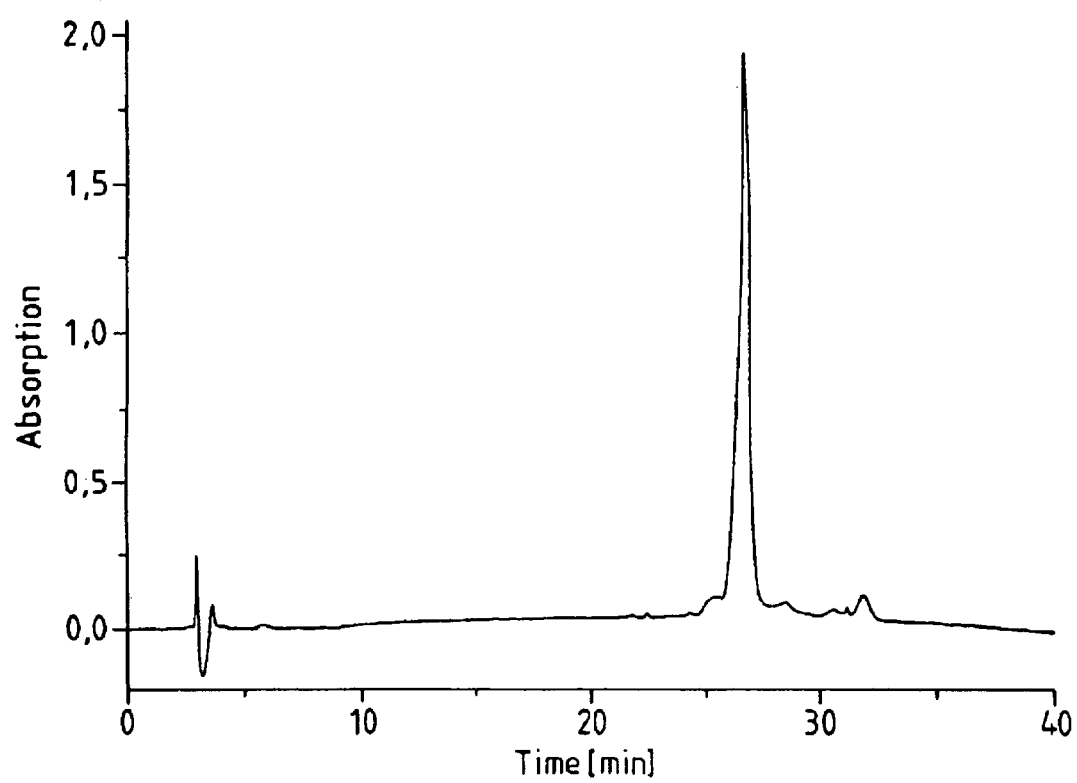

FIG. 9: HPLC chromatogram of the linear, deprotected dodecapeptide (crude product after removal from the resin; Example 6).

Figure 10:
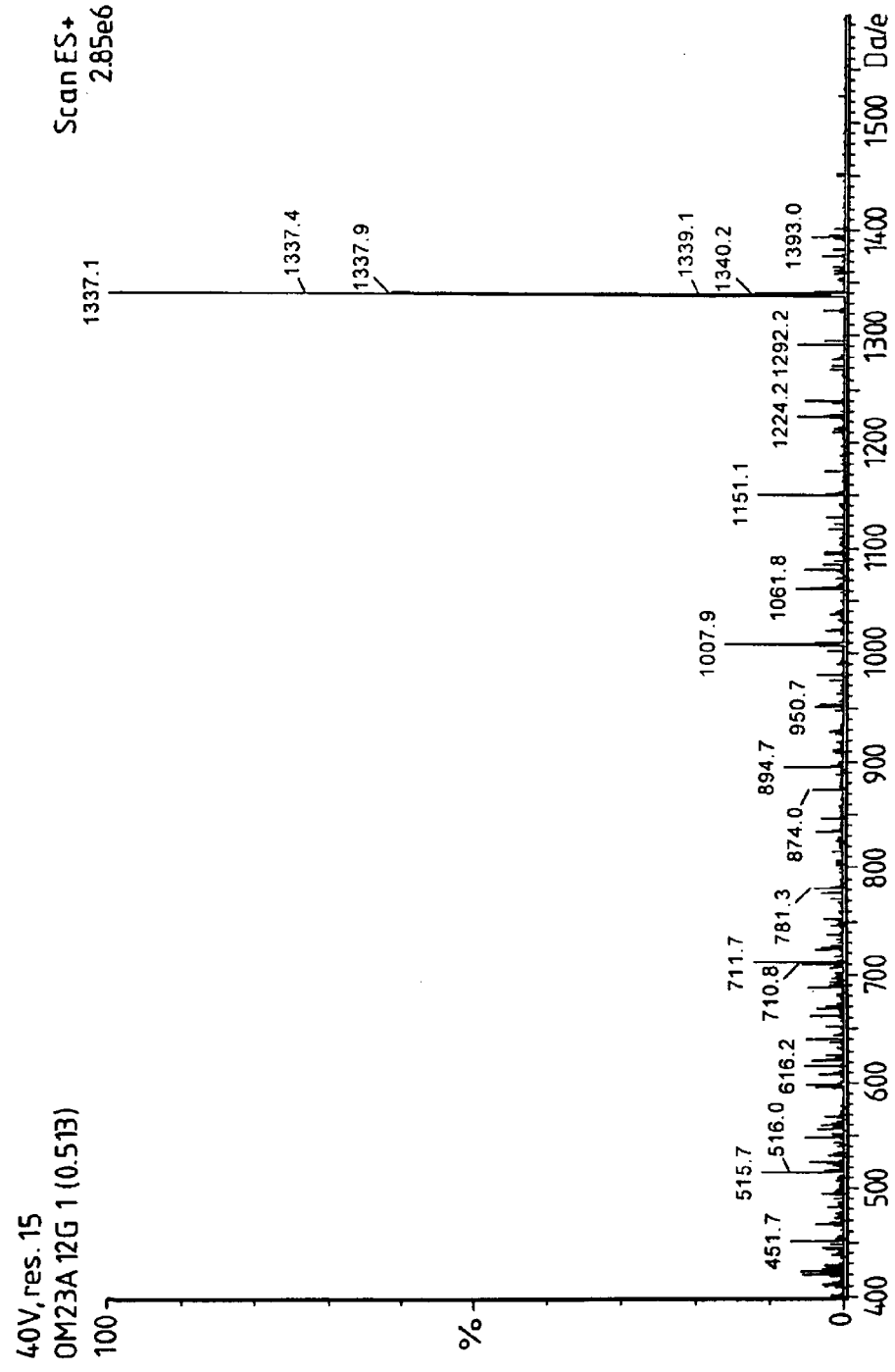

FIG. 10: ESI mass spectrum of the linear, deprotected dodecapeptide (crude product after removal from the resin; Example 6).

Figure 11:
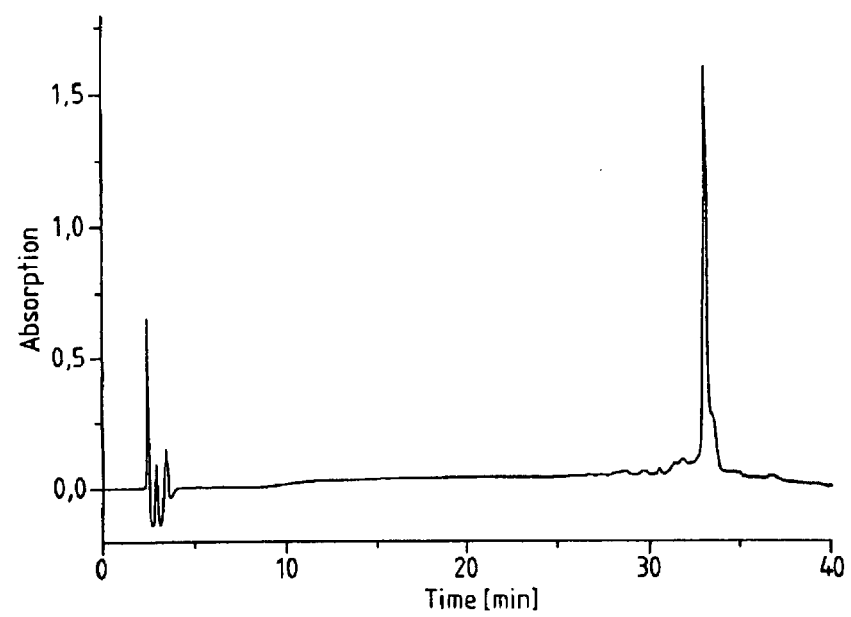

FIG. 11: HPLC chromatogram of the crude product of the cyclization reaction (Example 6).

FIG. 12: HPLC chromatogram of the purified final product, omphalotin A (Example 6).

Figure 13:
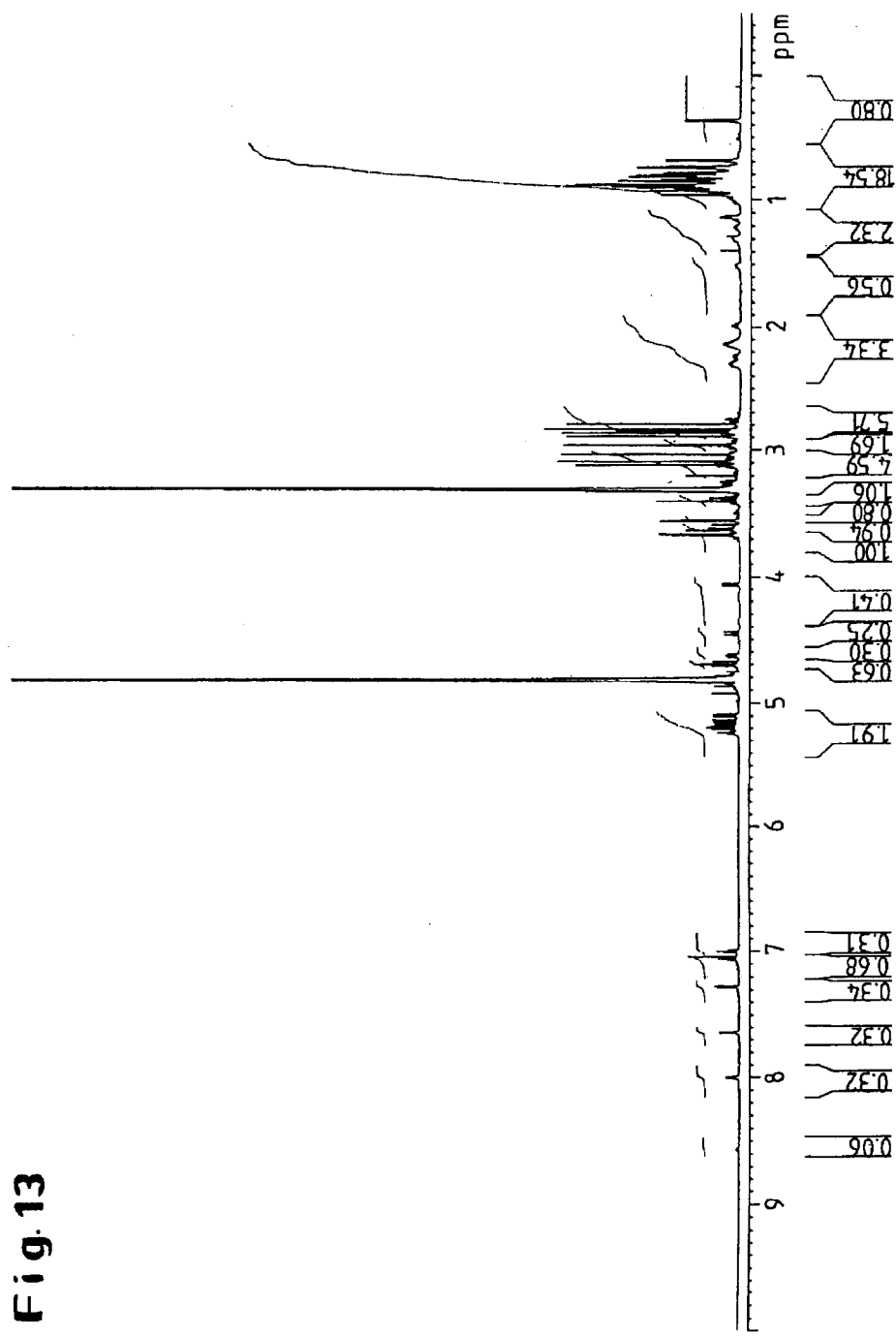
Figure 14:
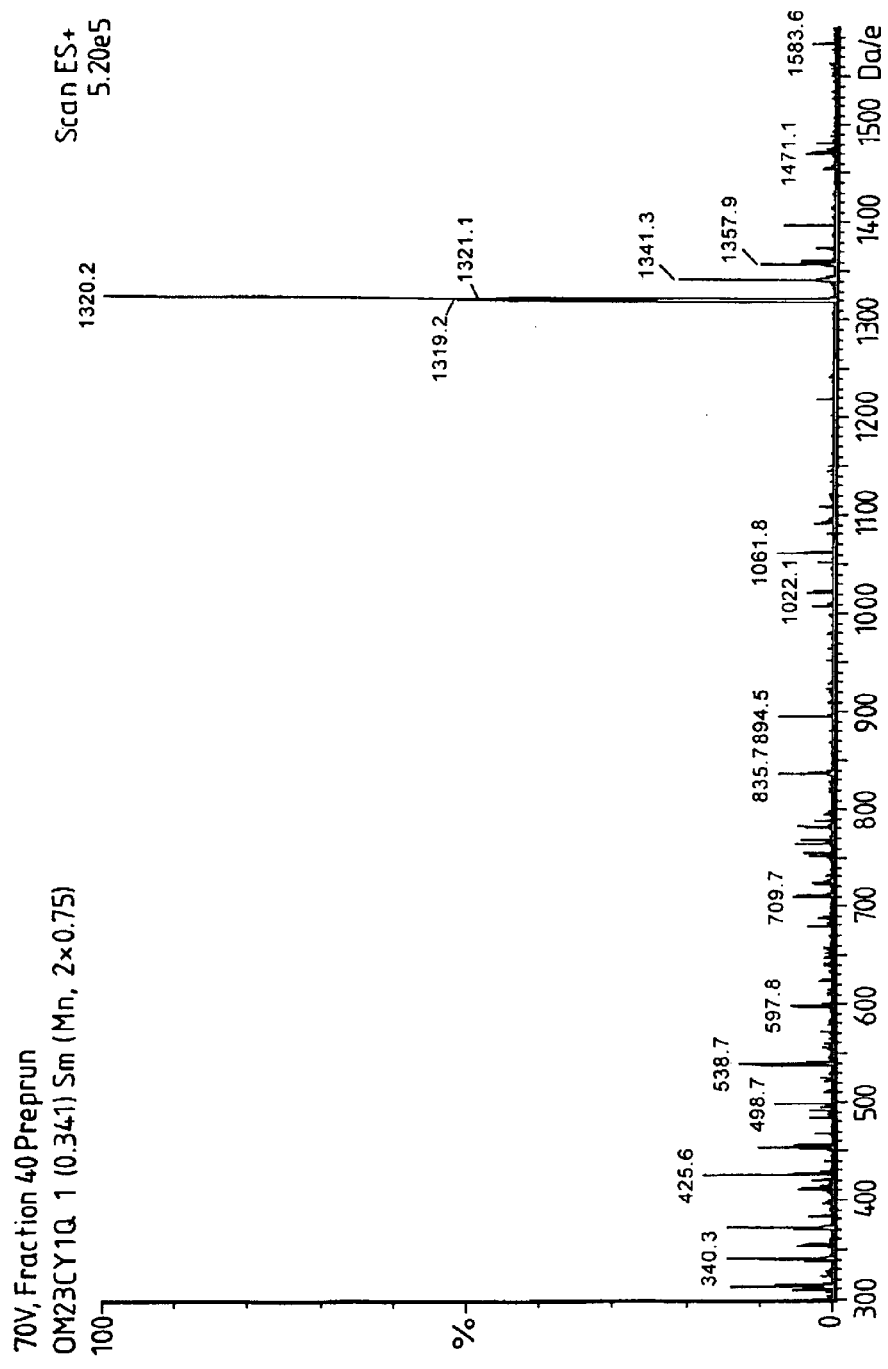

FIG. 13: $^1$H-NMR (700 MHz, CD$_3$OD) of the purified final product, omphalotin A (Example 6).

FIG. 14: ESI mass spectrum of the purified final product, omphalotin A (Example 6).

Example 7

Improved Synthesis of Omphalotin A (V)

In order to avoid the problem of the epimerization of the C-terminal amino acid during the cyclization, the optically non-active amino acid Fmoc-sarcosine was coupled to the carrier polymer as the first amino acid. To this end, 200 mg of TCP resin (substitution 1.04 mmol/g) were treated with a solution of 1 eq. of Fmoc-Sar-OH and 3 eq. of DIEA in DCM(abs) and the suspension was shaken for 3 h. Approximately 0.5 ml of methanol was then added to the suspension in order to cap the remaining trityl chloride functions as methyl ethers. An Fmoc determination showed a coating of 0.58 mmol/g. Taking into account the theoretical mass increase of the resin of about 40 mg, this means that 0.14 mmol of Fmoc-sarcosine was immobilized on the synthesis resin. Based on this amount of substance, the following reagent excesses were employed for the BTC coupling:

| Fmoc-Amino acid: | 3.5 eq. |
| --- | --- |
| Triphosgene: | 1.15 eq. |
| Collidine: | 10.0 eq. |
| DIEA: | 8.0 eq. |

Triphosgene was prepared as a stock solution having a concentration of 61.5 mmol/l (corresponding to 18.27 mg of BTC per milliliter of THF(abs)), of which 5.36 ml were employed per mmol of amino acid. An amino acid concentration of 0.19 mol/l resulted from this.

The basic procedure in the triphosgene coupling is analogous to Example 6 apart from two exceptions:

1.) The addition of the now almost halved amount of DIEA to the deprotected peptidyl resin was carried out only immediately before the addition of the activating solution (Fmoc-amino acid, triphosgene, collidine in THF(abs)).
2.) The Fmoc deprotection of the peptidyl resin using piperidine was kept as short as possible in terms of time, i.e. the Fmoc-protected resin was treated with 20% piperidine/DMF for 1×3 min and 1×8 min.

Both measures mentioned should minimize the contact of the Fmoc-deprotected resin with base, in order to suppress a base-catalysed nucleophilic attack of the free amino terminus on the trityl ester bond of the sarcosine and the cyclizing elimination resulting therefrom. This side reaction, which leads to the already mentioned formation of diketopiperazines at the dipeptide stage, is presumably responsible for the failure of earlier attempts at synthesis of omphalotin A and shorter peptide segments with sarcosine as the C-terminal amino acid using the triphosgene coupling.

In some cases, the HOAt coupling was used, which was carried out as in Example 6. Furthermore, in some cases the HATU coupling was used. In this, the procedure was as follows: The Fmoc-amino acid to be coupled (3.5 eq.) was weighed in together with HATU (3.5 eq.) and dissolved in an amount of DCM(abs)/DMF(abs) (1:1) which was as small as possible. DIEA (7 eq.) was added to the solution and it was allowed to stand for 15 min for preactivation. This solution was then added directly to the deprotected peptidyl resin preswollen in DMF(abs) and shaken for the time indicated in each case. The reaction solution was filtered off with suction and the resin was washed with DMF, DCM, DMF, DCM, MeOH (in each case 3×).

The changes described made possible the synthesis of optically highly pure omphalotin A starting from TCP resin coated with Fmoc-Sar. In this process, each of the three sarcosines occurring in the target molecule was used as a C-terminal amino acid, which led to the following three different linear precursor molecules:

a.) H-Trp-MeVal-Ile-MeVal-MeVal-Sar-MeVal-MeIle-Sar-Val-MeIle-Sar-OH
b.) H-Val-MeIle-Sar-Trp-MeVal-Ile-MeVal-MeVal-Sar-MeVal-MeIle-Sar-OH
c.) H-MeVal-MeIle-Sar-Val-MeIle-Sar-Trp-MeVal-Ile-MeVal-MeVal-Sar-OH

While the linear dodecapeptides are obtained in very satisfactory purities in all three cases, the cyclization only proceeded quantitatively in cases a.) and b.); in case c.) approximately 20% of the linear peptide was still present in the final product.

By way of example, the synthesis variants will be shown here by means of the linear dodecapeptide b.).

Course of Synthesis:
1.) Coupling of MeIle->Sar: triphosgene, 3 h, chloranil test negative.
2.) Coupling of MeVal->MeIle: triphosgene, 3 h, chloranil test negative.
3.) Coupling of Sar->MeVal: triphosgene, 2.5 h, chloranil test negative.
4.) Coupling of MeVal->Sar: triphosgene, 3 h, chloranil test negative. HPLC purity:>98%.
5.) Coupling of MeVal->MeVal: triphosgene, 3 h, chloranil test weakly positive Recoupling triphosgene, 3 h, chloranil test negative. HPLC purity:>95%.
6.) Coupling of Ile->MeVal: HATU, 20 h, chloranil test weakly positive Recoupling HATU, 3 h, chloranil test weakly positive Recoupling HOAt, 16 h, chloranil test negative. HPLC purity: about 90%.
7.) Coupling of MeV->Ile: triphosgene, 3 h, HPLC purity: 90%.
8.) Coupling of Trp->MeV: HATU, 4 h, HPLC purity: 89%.
9.) Coupling of Sar->Trp: triphosgene, 4 h, HPLC purity: 86%.
10.) Coupling of MeIle->Sar: triphosgene, 4 h, HPLC purity: 83%.
11.) Coupling of Val->MeIle: HATU, 5 h, HPLC purity: 80%.

All HPLC purities indicated relate to the Fmoc-protected peptide ($\lambda$=214 nm). The prolonged reaction times of most BTC couplings result primarily from the parallel reaction procedure for the simultaneous synthesis of all three linear precursor peptides mentioned. A lowering of the coupling efficiency by the reduction of the amounts of reagents employed was not observed.

The racemization control of the omphalotin A (OmA) synthesized as in Example 7 was carried out as described under Example 6.

|  | N-Me-D-MeVal | N-Me-D-MeIle |
| --- | --- | --- |
| Linear dodecapeptide | 1.2% | 2.4% |
| OmA crude product | 1.5% | 3.2% |

As expected, the proportion of N-Me-D-MeIle in the cyclized crude product is not markedly increased in relation to the linear precursor peptide, as it is not involved in the cyclization reaction. These values and the peak sharpness of the cyclization product in the HPLC chromatograms (FIGS. 15 and 16) mean that the product purity of the omphalotin A synthesized as in Example 7 must be markedly better than that of the product obtained as in Example 6. The HPLC chromatogram of the purified compound (FIG. 17) confirmed this. A purification by means of preparative HPLC yielded the highly pure product in a total yield of 21%.

Figure 15:
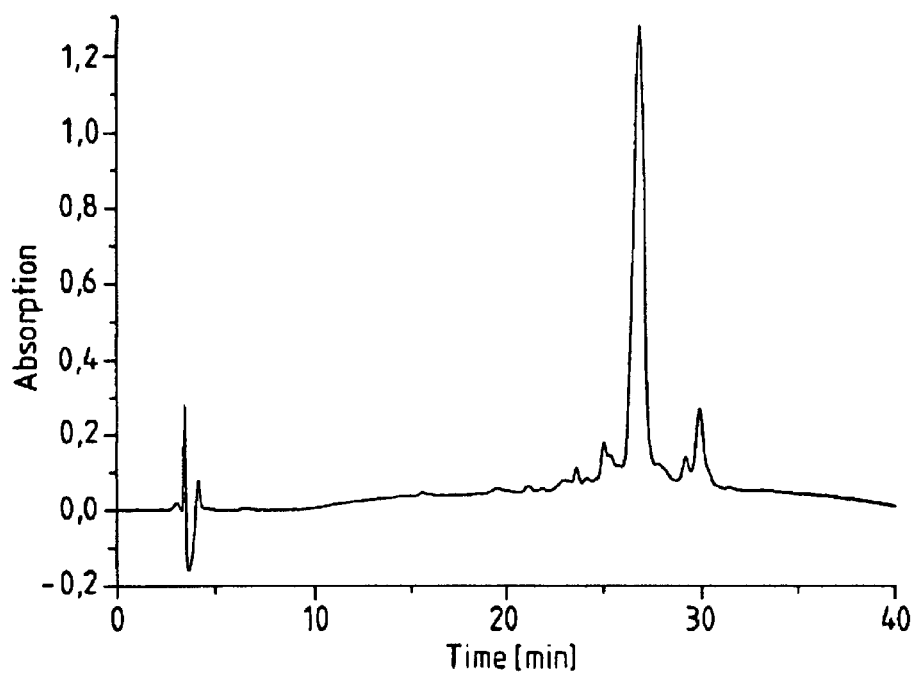

FIG. 15: HPLC chromatogram of the Fmoc-deprotected, linear dodecapeptide (Example 7).

Figure 16:
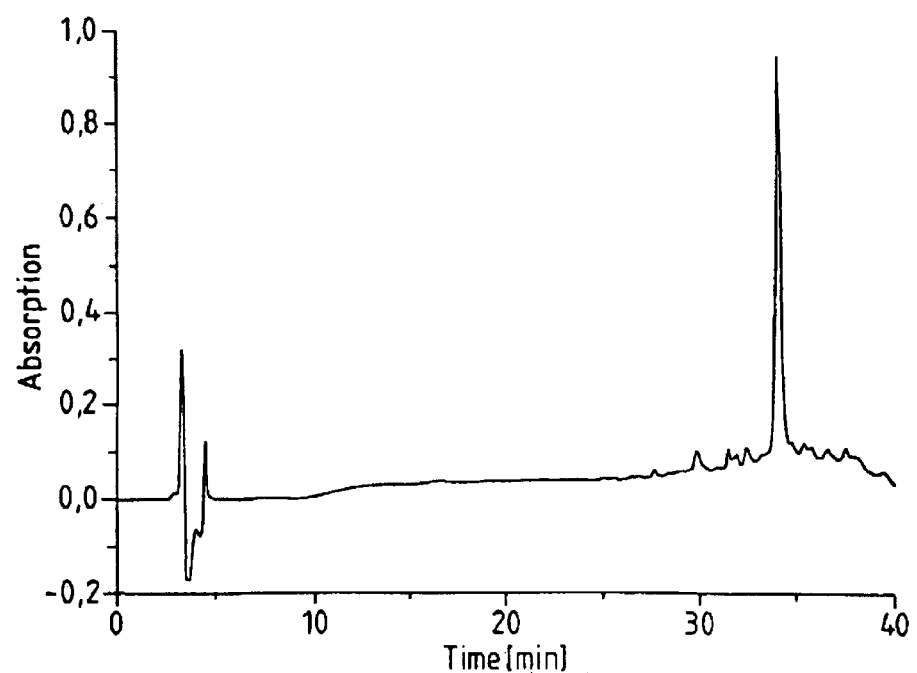

FIG. 16: HPLC chromatogram of the crude product of the cyclization reaction (Example 7).

Figure 17:
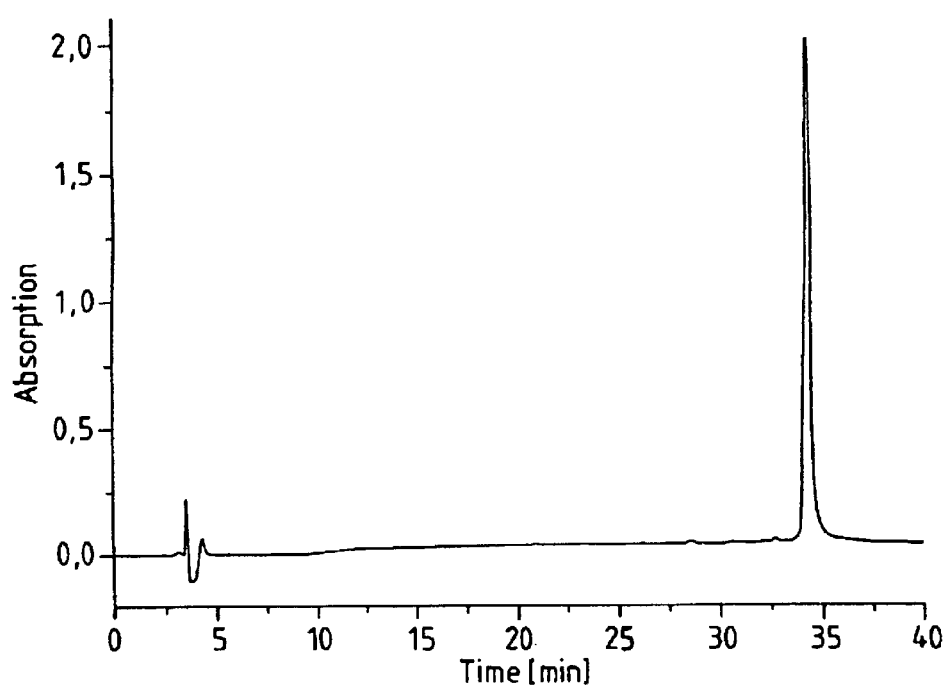

FIG. 17: HPLC chromatogram of the purified, optically pure omphalotin A (Example 7).

What is claimed is:

1. A process for the preparation of carboxamides from an acid component in the form of a compound having at least one carboxyl groups and an amine component in the form of a compound having at least one primary or secondary amino group, comprising the following steps:

i) introducing the amine component into a solvent together with a coupling base in the form of a sterically hindered trialkyl amine, ii) adding the acid component to a solvent with an activating reagent in the form of a carbonate of the formula I,

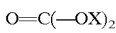

which contains the two identical or different electron-withdrawing groups X which are separate or connected to one another,
or its monohalide of the formula II,

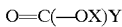

in which X has the same meaning as in formula I and Y represents a halogen atom,
or its dihalide of the formula III,

in which Y and Y' independently of one another each represent a halogen atom,
and an activating base in the form of a sterically hindered momo- or polyalkyl-substituted pyridine and (iii) adding the mixture containing the acid component as in (ii) to the mixture containing the amino component as in (i).

2. The process according to claim 1, characterized in that the acid component and/or the amine component is an amino acid or a peptide, whose other carboxyl and/or amino groups are protected.

3. The process according to claim 2, characterized in that
a) the acid component and the amine component are identical or different amino acids, or
b) the acid component is an amino acid and the amine component is a peptide, or
c) the amine component is an amino acid and the acid component is a peptide,
where, when there is at least one carboxyl group and at least one primary or secondary amino group, further carboxyl and primary or secondary amino groups present are protected.

4. The process according to claim 3, characterized in that the amino group of the amine component is a secondary amino group and/or the amino group bonded to the α-C atom of the acid component is a tertiary amino group.

5. The process according to one of claims 1 to 4, characterized in that the amine component or the acid component is reversibly bound to a solid phase.

6. The process according to one of claims 1 to 4, characterized in that the acid component and the amine component are employed in a ratio of molar equivalents of at least 1:1.

7. The process according to one of claims 1 to 4, characterized in that the acid component and the activating reagent are employed in a ratio of molar equivalents of at least 1:1.

8. The process according to one of claims 1 to 4, characterized in that the coupling base and/or the activating base are employed in a ratio to the amine component of molar equivalents of at least 2:1.

9. The process according to one of claims 1 to 4, characterized in that
a carbonate of the fonnula I, in which one or both groups X independently of one another represent a group $CH_{3-n}Y_n$, where n represents one of the numbers 1, 2 or 3 and $Y_n$ represents one, two or three identical or different halogen atoms, or
a halogenated 1,3-dioxolan-2-one derivative, whose four hydrogen atoms in the 4- and 5-position are completely or partially substituted by one, two, three or four identical or different halogen atoms, or
a monohalide of the formula II, in which X is a group $CH_{3-n}Y_n$, where n represents one of the numbers 1, 2 or 3 and $Y_n$ represents one, two or three identical or different halogen atoms, or
a dihalide of the formula III
is employed as activating reagent.

10. The process according to one of claims 1 to 4, characterized in that the solvents are selected independently of one another from tetrahydrofuran, 1,4-dioxane, tetrahydropyran, ethylene glycol dimethyl ether, diethylene glycol dimethyl ether, trichioromethane, 1,3-dichloropropane, 1,2-dichloroethane and nitromethane, or a mixture of two or more thereof.

11. The process according to claim 4, characterized in that the amino group of the amine component and the protected or peptide-linked amino group of the acid component are both N-alkylated.

12. The process according to claim 11, characterized in that the amino group of the amine component and the protected or peptide-linked amino group of the acid component are N-alkylated independently of one another with a methyl, ethyl, propyl, isopropyl, cyclohexyl, or benzyl group.

13. The process according to claim 5, characterized in that the said solid phase is a resin selected from the group consisting of Wang polystyrene resin, Rink amide MBHA resin, and TCP resin.

14. The process according to claim 6, characterized in that said ratio is 1:1 to 10:1.

15. The process according to claim 6, characterized in that said ratio is 1:1 to 5:1.

16. The process according to claim 7, characterized in that said ratio is 1:1 to 4:1.

17. The process according to claim 7, characterized in that said ratio is 2:1 to 3:1.

18. The process according to claim 8, characterized in that said ratio is 4:1 to 30:1.

19. The process according to claim 8, characterized in that said ratio is 8:1 to 20:1.

20. The process according to claim 8, characterized in that said ratio is 12:1 to 16:1.

21. The process according to claim 9, characterized in that said group $CH_{3-n}Y_n$ is selected from the group consisting of $CCl_3$, $CF_3$, $CBr_3$, $CHCl_2$, $CHF_2$, $CHBr_2$, $CHI_2$,$CH_2CL$, $CH_2F$, and $CH_2Br$.

22. The process according to claim 9, characterized in that said activating agent is selected from the group consisting of triphosgene, diphosgene, phosgene, and 4,4,5,5-tetrachloro-1,3-dioxolan-2-one.

23. The process according to claim 1, characterized in that said pyridine derivative is selected from the group consisting of collidines, 2,4,6-tritert-butylpyridine, 2,6-ditert-butylpyridine, 2,6-ditert-butyl-4-methylpyridine, 2,6-dimethylpyridine, 2,3,5,6-tetramethylpyridine, and 2-methylpyridine.

24. The process according to claim 1, characterized in that said trialkylamine is selected from the group consisting of diisopropylethylamine, triisopropylamine, N-methylmorpholine, and triethylamine.

25. The process according to claim 1, characterized in that said coupling base is diisopropylethylamine or triisopropylamine.

26. The process according to claim 1, characterized in that said activating base is selected from the group consisting of 2,4,6-collidine, 2,4,6-tritert-butylpyridine, 2,6-ditert-butylpyridine, 2,6-ditert-butyl-4-methylpyridine, 2,6-dimethylpyridine, and 2,3,5,6-tetrarnethylpyridine.

* * * * *